(12) United States Patent
Zhang et al.

(10) Patent No.: US 11,661,615 B2
(45) Date of Patent: May 30, 2023

(54) BIOSYNTHESIS METHOD WITH HOST CELL AND QUALITY CONTROL SYSTEM

(71) Applicant: WASHINGTON UNIVERSITY, St. Louis, MO (US)

(72) Inventors: Fuzhong Zhang, St. Louis, MO (US); Yi Xiao, St. Louis, MO (US)

(73) Assignee: Washington University, St. Louis, MO (US)

( * ) Notice: Subject to any disclaimer, the term of this patent is extended or adjusted under 35 U.S.C. 154(b) by 224 days.

(21) Appl. No.: 15/757,212

(22) PCT Filed: Sep. 2, 2016

(86) PCT No.: PCT/US2016/050146
§ 371 (c)(1),
(2) Date: Mar. 2, 2018

(87) PCT Pub. No.: WO2017/040958
PCT Pub. Date: Mar. 9, 2017

(65) Prior Publication Data
US 2018/0273989 A1   Sep. 27, 2018

Related U.S. Application Data

(60) Provisional application No. 62/214,248, filed on Sep. 4, 2015.

(51) Int. Cl.
*C12N 15/66*  (2006.01)
*C12P 7/6409*  (2022.01)
*C12N 15/63*  (2006.01)
*C12P 13/22*  (2006.01)

(52) U.S. Cl.
CPC ............ *C12P 7/6409* (2013.01); *C12N 15/63* (2013.01); *C12P 13/22* (2013.01); *C12P 13/225* (2013.01)

(58) Field of Classification Search
None
See application file for complete search history.

(56) References Cited

U.S. PATENT DOCUMENTS

2013/0059295 A1   3/2013   Zhang et al.

FOREIGN PATENT DOCUMENTS

WO   2013180810 A1   12/2013

OTHER PUBLICATIONS

Michener et al. (Metabolic Engin., vol. 14, 2012, pp. 212-222).*
Qian et al. (Current Opinion in Chemical Engineering, vol. 14, pp. 93-102, 2016).*
Palaniappan et al. (J. of Clinical Microbiology, Apr. 2006, vol. 44, No. 4, pp. 1495-1501).*
Zhang et al. (Metabolic Engineering, vol. 14, 2012, pp. 653-660).*
Zhang et al. (Nature Biotechnology, vol. 30, No. 4, 2012, pp. 354-360).*
International Search Report and Written Opinion for International Application No. PCT/US2016/050146, dated Dec. 8, 2016, 7 pages.
Raman et al. Evolution-guided optimization of biosynthetic pathways, PNAS, 2014, vol. 111, No. 50, pp. 17803-17808.
Xiao et al. Exploiting nongenetic cell-to-cell variation for enhanced biosynthesis, Nature Chemical Biology, 2016, vol. 12, pp. 339-344.
Xiao et al. Supplemental material. Exploiting nongenetic cell-to-cell variation for enhanced biosynthesis, Nature Chemical Biology, 2016, vol. 12, pp. 339-344.
Zhang et al. Supplemental material. Design of a dynamic sensor-regulator system for production of fatty acid-based chemicals and fuels, Nature Biotechnology, 2012, vol. 30, No. 4, pp. 354-359.
Liu et al. Applications and advances of metabolite biosensors for metabolic engineering, Metabolic Engineering, 2015, vol. 31, pp. 35-43.

* cited by examiner

*Primary Examiner* — Hope A Robinson
(74) *Attorney, Agent, or Firm* — Armstrong Teasdale LLP

(57) ABSTRACT

Systems, methods, and host cells utilizing a PopQC construct for enhancing product biosynthesis by exploitation of non-genetic cell-to-cell variation are disclosed. The PopQC construct includes at least a product-responsive biosensor and a selection gene.

8 Claims, 48 Drawing Sheets

| Strains | Descriptions | Genotype[1] |
|---|---|---|
| DH10B | Host cell for FFA production or cloning | F- endA1 recA1 galE15 galK16 nupG rpsL ΔlacX74 Φ80lacZΔM15 araD139 Δ(ara,leu)7697 mcrA Δ(mrr-hsdRMS-mcrBC) λ- |
| DH1 | Host cell (with a fadE gene deletion) for FFA production. Gene fadE encodes an acyl-CoA dehydrogenase, which is involved in FA degradation (β-oxidation). | endA1 recA1 gyrA96 thi-1 glnV44 relA1 hsdR17($r_K^-$ $m_K^+$) λ- ΔfadE |
| MG1655 | Host cell for tyrosine production | F- λ- ilvG- rfb-50 rph-1 |
| TES | FFA-producing strain used for cell-to-cell variation studies | DH1/pA5c-tesA[2] |
| $BS_{AR}$ | FFA biosensor strain with $P_{AR}$ promoter (RFP as output) | DH1/pE8a-fadR+pBARk-rfp |
| $BS_{AR1/2/3}$ | FFA biosensor control strains with promoters $P_{AR1/2/3}$, respectively (RFP as output) | DH1/pE8a-fadR+pBAR1/2/3k-rfp |
| $QC_{FAT}$ | PopQC strain with Tc-resistance gene tetA under the control of $P_{AR}$ | DH1/pE8a-fadR+pBARk-tetA-rfp |
| $QC_{FAT+}$ | FFA-producing strain harboring $P_{AR}$-PopQC | DH1/pE8a-fadR+pBARk-tetA-rfp+pA5c-tesA |
| $QC_{FAT-}$ | FFA-producing strain without PopQC (tetA in $QC_{FAT+}$ was omitted) | DH1/pE8a-fadR+pBARk-rfp+pA5c-tesA |
| $QC_{FAT+1/2/3}$ | FFA-producing strains harboring inactive PopQC ($P_{AR}$ in $QC_{FAT+}$ was replaced by promoters $P_{AR1}$, $P_{AR2}$, or $P_{AR3}$) | DH1/pE8a-fadR+pBAR1/2/3k-tetA-rfp+pA5c-tesA |
| $QC_{FAT+G}$ | FFA-producing strain harboring $P_{AR}$-PopQC and GFP | DH1/pE8a-fadR+pBARk-tetA-gfp+pA5c-tesA |
| $QCN^3$ (N=1,2,...25) | Offspring colonies isolated from non-Tc culture of strain $QC_{FAT+}$ during the FFA production process | DH1/pE8a-fadR+pBARk-tetA-rfp+pA5c-tesA |
| QCTcN# (N=1,2,...35) | Offspring colonies isolated from Tc culture of strain $QC_{FAT+}$ during the FFA production process | DH1/pE8a-fadR+pBARk-tetA-rfp+pA5c-tesA |
| $QC_{FAL+}$ | FFA-producing strain harboring $P_{AR}$-PopQC with tetA in $QC_{FAT+}$ replaced by leuABCD | DH10B/pE8a-fadR+pBARk-LeuABCD-rfp+pA5c-tesA |
| $QC_{FAL-}$ | FFA-producing strain. Compared to $QC_{FAL+}$, the genes leuABCD were omitted. | DH10B/pE8a-fadR+pBARk-rfp+pA5c-tesA |
| $BS_{T0/1/2}$ | Tyrosine biosensor strains with promoters $P_{T0}$, $P_{T1}$, or $P_{T2}$ (RFP as output) | MG1655/pE8a-tyrR+pBT0/1/2k-rfp |
| $QC_{TYT1+/2+}$ | Tyrosine producing strains harboring PopQC using $P_{T1}$ or $P_{T2}$ to regulate tetA | MG1655/pE8a-tyrR+pBT1/2k-tetA-rfp+pA5c-tyr |
| $QC_{TYT0+}$ | Tyrosine producing strain. Compared to $QC_{TYT1+}$, $P_{T1}$ was replaced by $P_{T0}$. | MG1655/pE8a-tyrR+pBT0k-tetA-rfp+pA5c-tyr |

FIG. 1

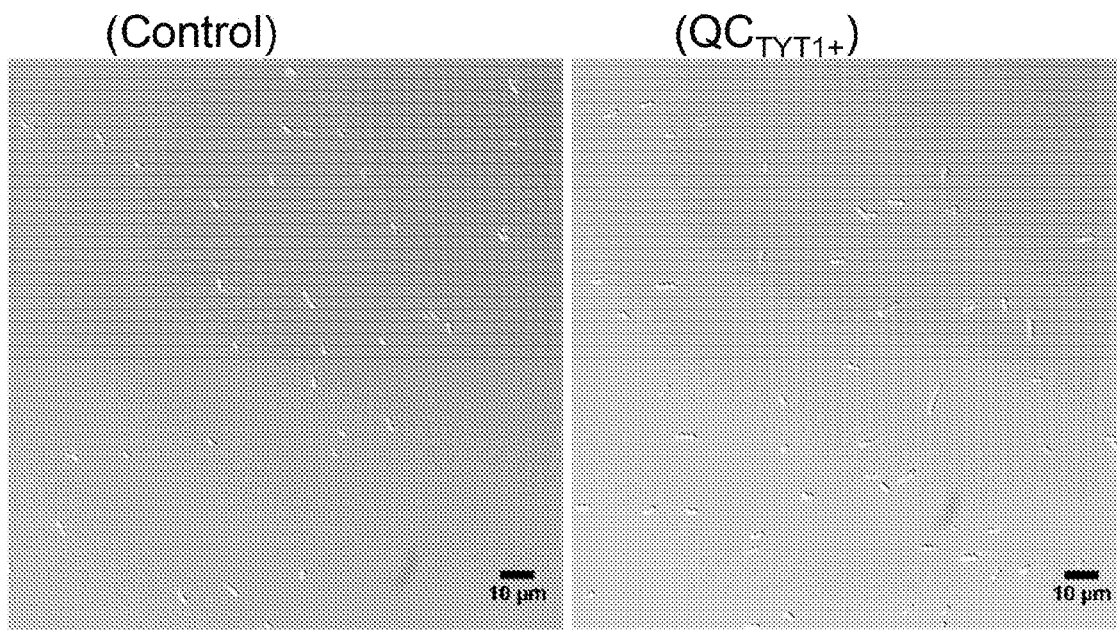
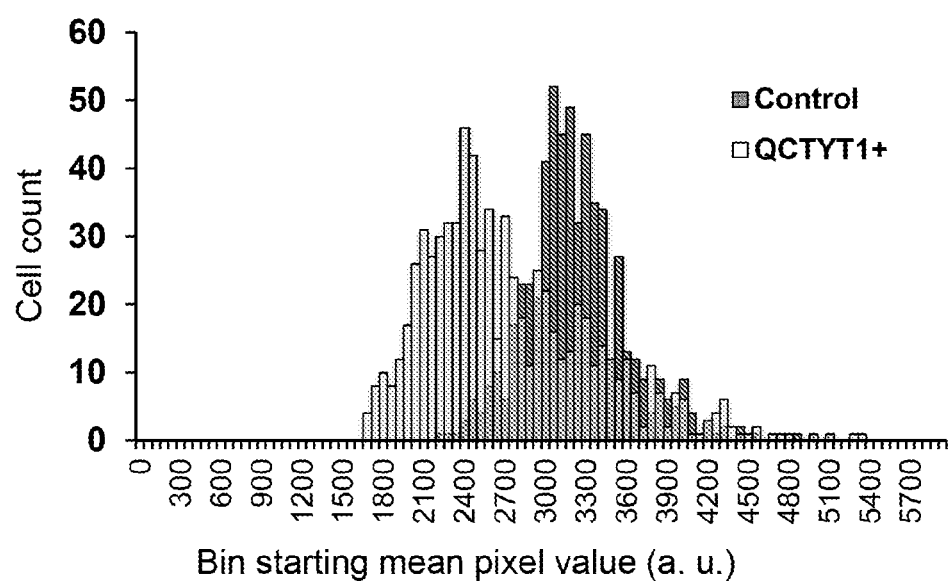
FIG. 2B

| Plasmids | Descriptions (Antibiotic, rep. origin, promoter, expressing genes, (regulator)) |
|---|---|
| pA5c-tesA | FA producing plasmid (Cm$^r$, p15a, P$_{lacUV5}$, tesA, (LacI)) |
| pE8a-fadR | FadR expressing plasmid (Amp$^r$, ColE1, P$_{BAD}$, fadR, (AraC)) |
| pBARk-rfp | FA biosensor plasmid (Kan$^r$, pBBR1, P$_{AR}$, rfp) |
| pBAR1k-rfp | FA biosensor plasmid, as a control (Kan$^r$, pBBR1, P$_{AR1}$, rfp) |
| pBAR2k-rfp | FA biosensor plasmid, as a control (Kan$^r$, pBBR1, P$_{AR2}$, rfp) |
| pBAR3k-rfp | FA biosensor plasmid, as a control (Kan$^r$, pBBR1, P$_{AR3}$, rfp) |
| pBARk-tetA-rfp | PopQC plasmid (Kan$^r$, pBBR1, P$_{AR}$, tetA/rfp) |
| pBAR1k-tetA-rfp | PopQC plasmid, as a control (Kan$^r$, pBBR1, P$_{AR1}$, tetA/rfp) |
| pBAR2k-tetA-rfp | PopQC plasmid, as a control (Kan$^r$, pBBR1, P$_{AR2}$, tetA/rfp) |
| pBAR3k-tetA-rfp | PopQC plasmid, as a control (Kan$^r$, pBBR1, P$_{AR3}$, tetA/rfp) |
| pBARk-tetA-gfp | PopQC plasmid (Kan$^r$, pBBR1, P$_{AR}$, tetA/gfp) |
| pBARk-leuABCD-rfp | PopQC plasmid (Kan$^r$, pBBR1, P$_{AR}$, LeuABCD/rfp) |
| pE8a-tyrR | TyrR expressing plasmid (Amp$^r$, ColE1, P$_{BAD}$, tyrR, (AraC)) |
| pA5c-tyr | Tyrosine producing plasmid (Cm$^r$, p15a, P$_{lacUV5}$, aroG*/tyrB/tyrA*/aroC; Ptrc, aroA/ aroL, (LacI) ) |
| pBT0k-rfp | Tyrosine biosensor plasmid, as a control (Kan$^r$, pBBR1, P$_{T0}$, rfp) |
| pBT1k-rfp | Tyrosine biosensor plasmid (Kan$^r$, pBBR1, P$_{T1}$, rfp) |
| pBT2k-rfp | Tyrosine biosensor plasmid (Kan$^r$, pBBR1, P$_{T2}$, rfp) |
| pBT0k-tetA-rfp | PopQC plasmid, as a control (Kan$^r$, pBBR1, P$_{T0}$, tetA/rfp) |
| pBT1k-tetA-rfp | PopQC plasmid (Kan$^r$, pBBR1, P$_{T1}$, tetA/rfp) |
| pBT2k-tetA-rfp | PopQC plasmid (Kan$^r$, pBBR1, P$_{T2}$, tetA/rfp) |

FIG. 3

| Names | Sequences | Characterizations |
|---|---|---|
| aroP1 | TGTAAGTTTGCAATTCCG | Weak box from the promoter of gene aroP ($P_{aroP}$) |
| tyrP2 | TGTACATTTATATTTACA | Strong box from the promoter of gene tyrP ($P_{tyrP}$) |
| mtr1 | TGTAAAATAATATATACA | Strong box from the promoter of gene mtr ($P_{mtr}$) |
| mtr2 | CGTAATCATCGCTGAACA | Weak box from the promoter of gene mtr ($P_{mtr}$) |

FIG. 4

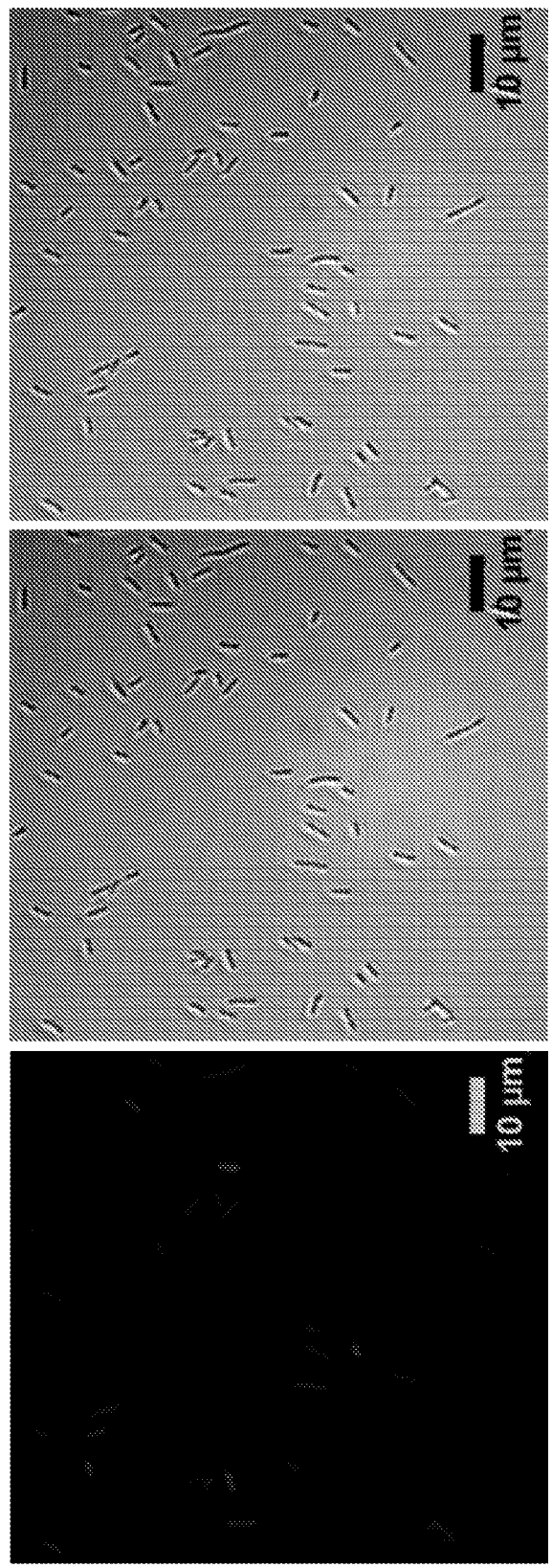

|  | Supernatant (g/L) | Whole cell culture (g/L) | Ratio (%) |
|---|---|---|---|
| Fatty acid |  |  |  |
| Strain QC$_{FAT+}$ | <0.02 | 1.11 | <2% |
| Tyrosine |  |  |  |
| Strain QC$_{TYT1+}$ | 0.3 | 0.37 | 81% |

FIG. 10

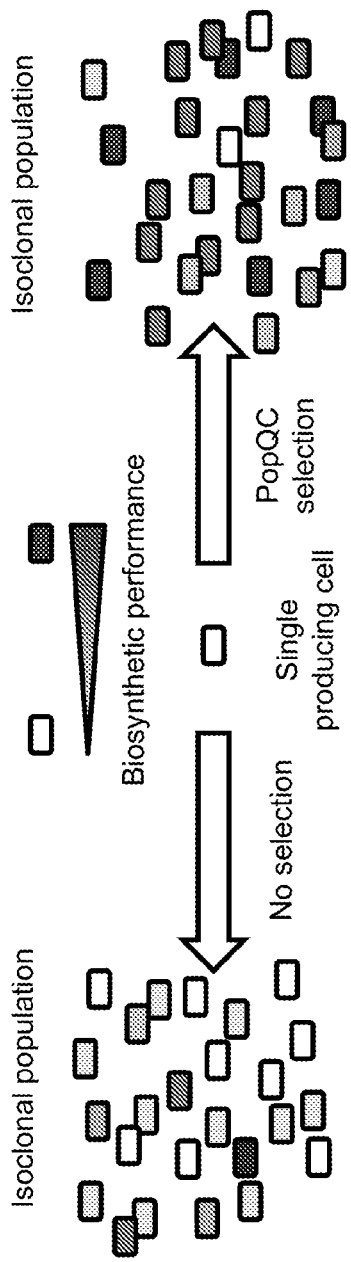
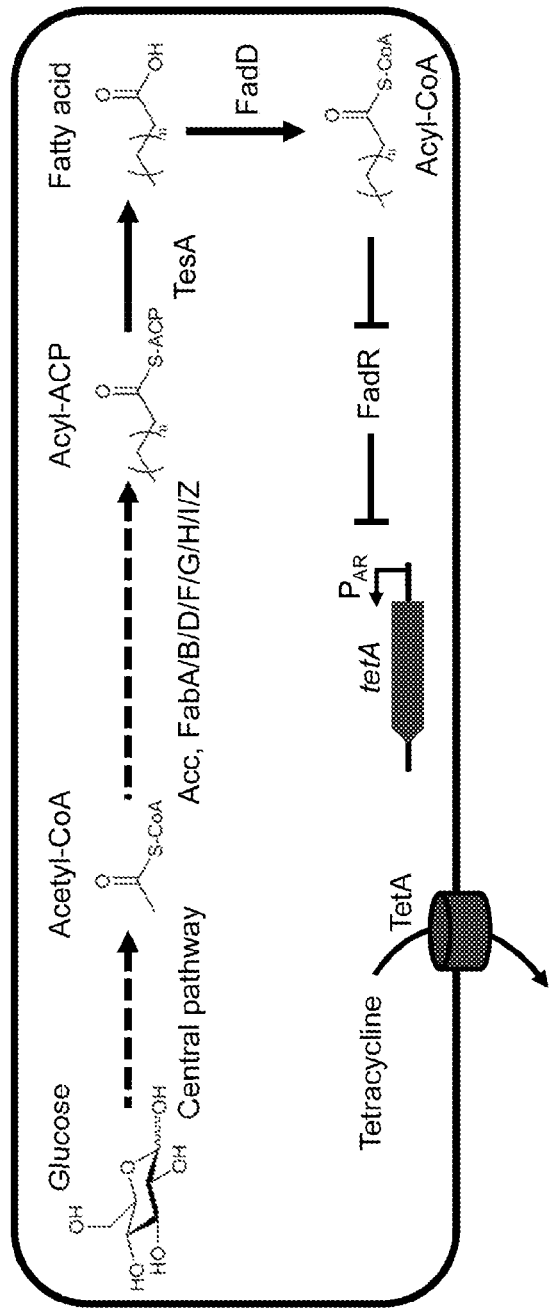
FIG. 12

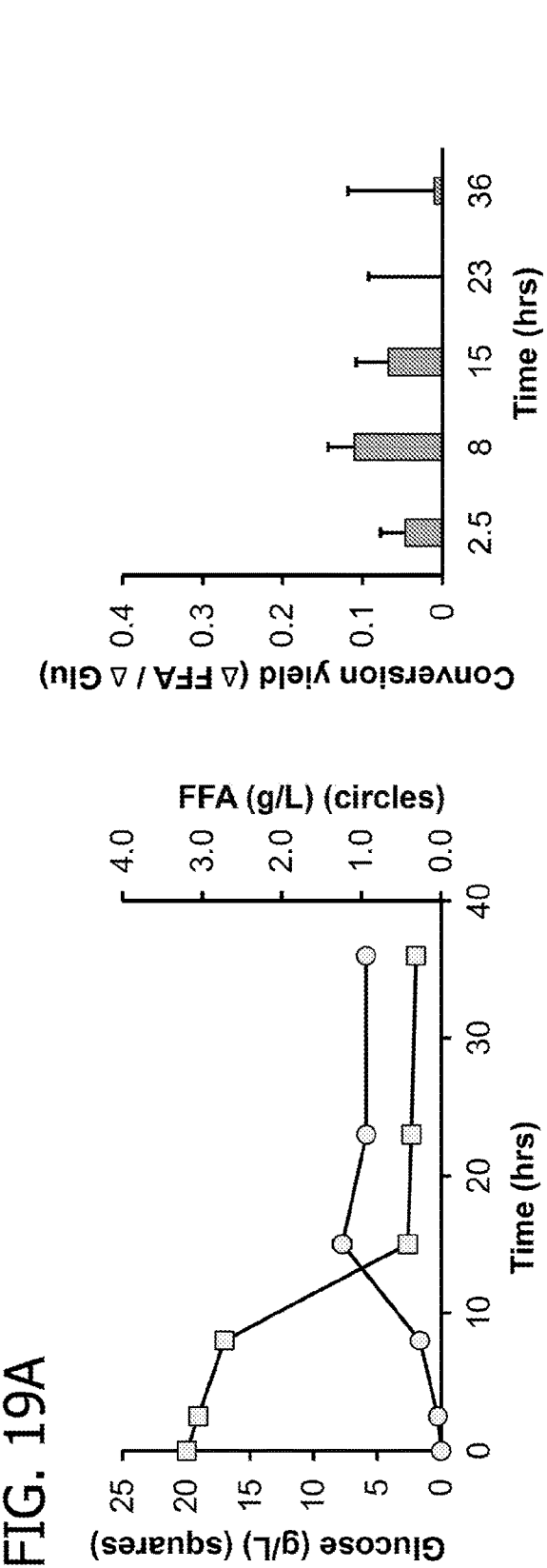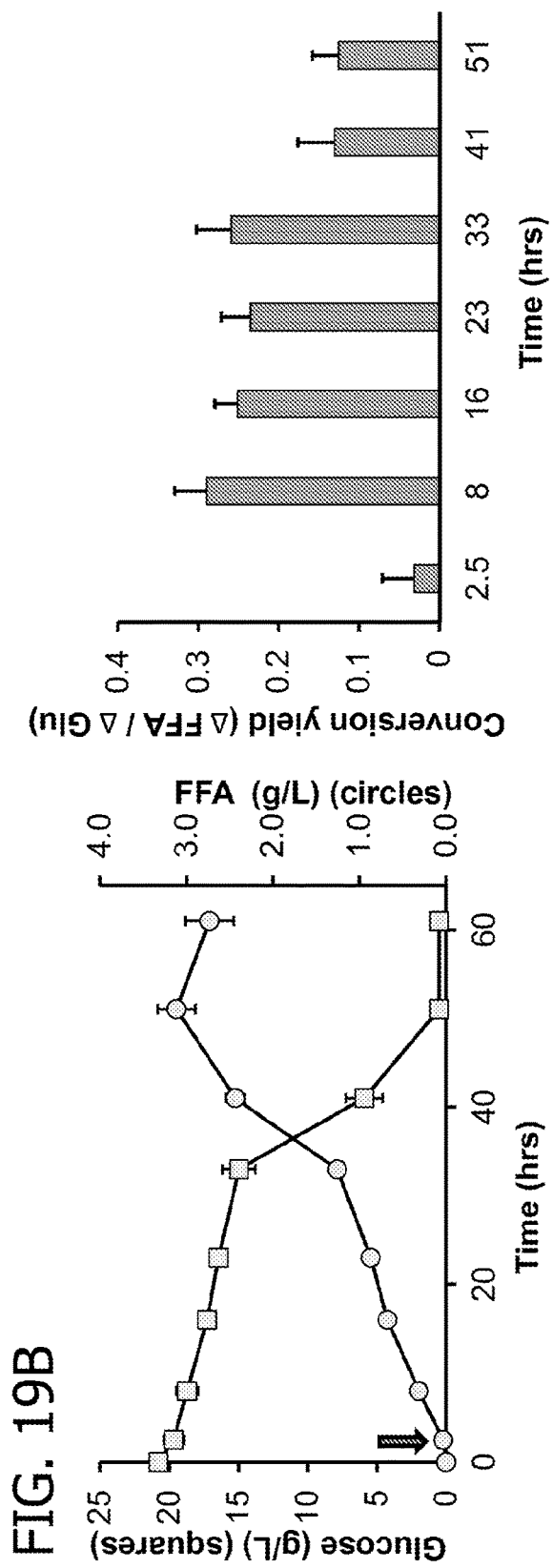
FIG. 19A
FIG. 19B

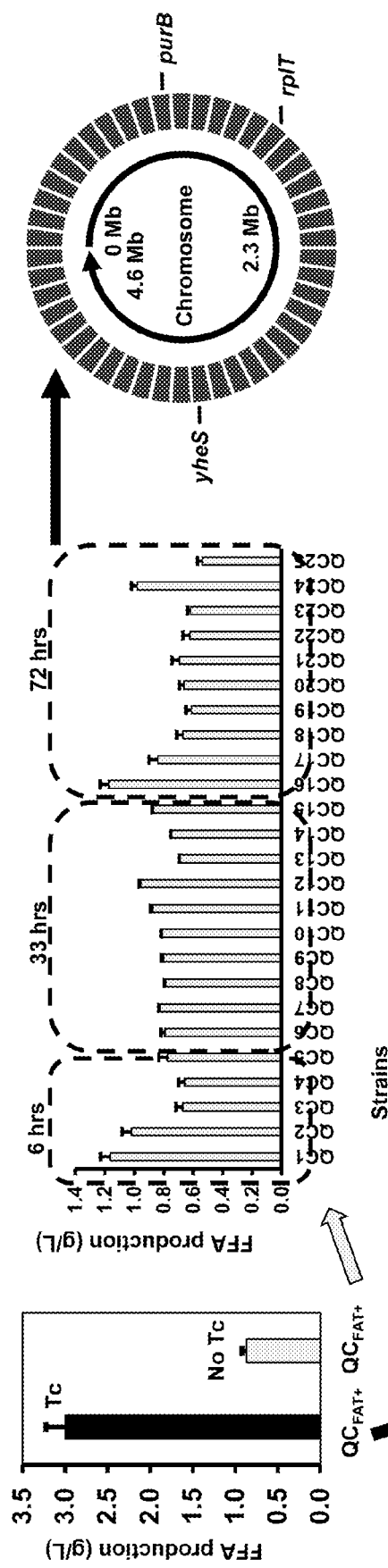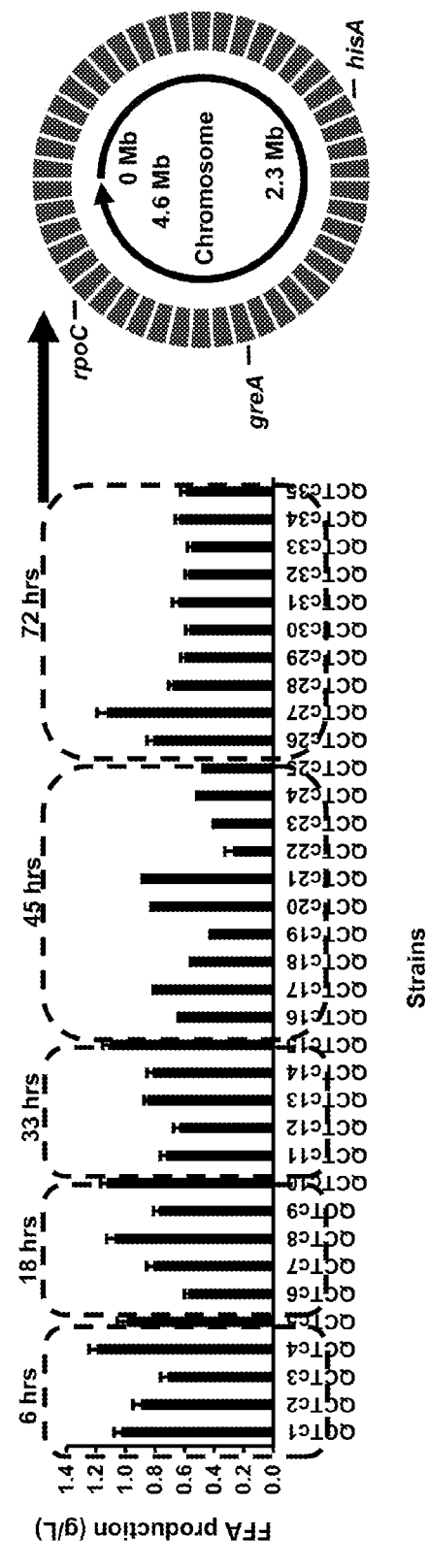
FIG. 21A
FIG. 21B

| E. coli strain QC\_x\_x\_x\_ Summary of changes by type | | E. coli strain QC\_x\_x\_x\_ SNPs detail | | | |
|---|---|---|---|---|---|
| | | Location (chromosome) | Gene(Description) | Nucleotide (reference/ deviation) | effect | Amino acid (old/new) |
| SNP | 11 | 1514876 | ykfC (Transposase IS4 family protein) | G/R | SYNONYMOUS_CODING | E/E |
| MNP | 0 | 2231623 | cirA (Colicin I receptor) | T/K | SYNONYMOUS_CODING | A/A |
| INS | 0 | 239229 | yafP (Transposase IS4 family protein) | A/M | SYNONYMOUS_CODING | A/A |
| DEL | 1 | 2845077 | rpoS (RNA polymerase sigma factor) | G/A | NON_SYNONYMOUS_CODING | T/I |
| MIXED | 0 | 3531168 | malT (ATP-dependent transcriptional activator) | T/G | NON_SYNONYMOUS_CODING | V/G |
| Interval | 0 | 3602338 | yhhI (Putative transposase) | A/R | NON_SYNONYMOUS_CODING | T/T or A |
| | | 3603087 | yhhI (Putative transposase) | C/M | SYNONYMOUS_CODING | S/S |
| | | 3603575 | yhhI (Putative transposase) | C/Y | SYNONYMOUS_CODING | D/D |
| | | 3603587 | yhhI (Putative transposase) | G/S | SYNONYMOUS_CODING | L/L |
| | | 227507 | ybfL (Predicted transposase, truncated) | G/R | SYNONYMOUS_CODING | G/G |
| | | 227792 | ybfL (Predicted transposase, truncated) | C/Y | SYNONYMOUS_CODING | F/F |

FIG. 22A

| E. coli strain QC16 Summary of changes by type | | E. coli strain QC16 SNPs detail | | | | |
|---|---|---|---|---|---|---|
| | | Location (chromosome) | (Gene Description) | Nucleotide reference (deviation) | effect | Amino acid (address) |
| SNP | 11 | 1514876 | ydeL (Transposase IS4 family protein) | G/R | SYNONYMOUS_CODING | E/E |
| MNP | 0 | 1783123 | rpIT (50S ribosomal protein L20) | C/S | NON_SYNONYMOUS_CODING | R/R to P |
| INS | 0 | 239229 | yafF (Transposase IS4 family protein) | A/M | SYNONYMOUS_CODING | A/A |
| DEL | 1 | 2843077 | rpoS (RNA polymerase sigma factor) | G/A | NON_SYNONYMOUS_CODING | T/I |
| MIXED | 0 | 3531168 | msrT (ATP-dependent transcriptional activator) | T/G | NON_SYNONYMOUS_CODING | V/G |
| Interval | 0 | 3602338 | ybhl (Putative transposase) | A/R | NON_SYNONYMOUS_CODING | T/T or A |
| | | 3603087 | ybhl (Putative transposase) | C/M | SYNONYMOUS_CODING | S/S |
| | | 3603373 | ybhl (Putative transposase) | C/Y | SYNONYMOUS_CODING | D/D |
| | | 3603387 | ybhl (Putative transposase) | G/S | SYNONYMOUS_CODING | L/L |
| | | 227507 | ybhL (Predicted transposase, truncated) | G/R | SYNONYMOUS_CODING | G/G |
| | | 227702 | ybhL (Predicted transposase, truncated) | C/Y | SYNONYMOUS_CODING | E/E |

FIG. 22B

E. coli strain QC17

SNPs detail

| Summary of changes by type | | Location (chromosome) | Gene(Description) | Nucleotide reference (deviation) | effect | Amino acid (old/new) |
|---|---|---|---|---|---|---|
| SNP | 9 | 1518476 | ydcC (Transposase IS4 family protein) | G/R | SYNONYMOUS_CODING | E/E |
| MNP | 0 | 239229 | yaiP (Transposase IS4 family protein) | A/M | SYNONYMOUS_CODING | A/A |
| INS | 0 | 2845077 | rpoS (RNA polymerase sigma factor) | G/A | NON_SYNONYMOUS_CODING | T/I |
| DEL | 1 | 3331168 | malT (ATP-dependent transcriptional activator) | T/S | NON_SYNONYMOUS_CODING | V/G |
| MIXED | 0 | 3602338 | yhhI (Putative transposase) | A/R | NON_SYNONYMOUS_CODING | T/T or A |
| Interval | 0 | 3603087 | yhhI (Putative transposase) | C/M | SYNONYMOUS_CODING | S/S |
| | | 3603375 | yhhI (Putative transposase) | C/Y | SYNONYMOUS_CODING | D/D |
| | | 3603387 | yhhI (Putative transposase) | G/S | SYNONYMOUS_CODING | L/L |
| | | 727690 | yhhI (Predicted transposase, truncated) | T/W | SYNONYMOUS_CODING | L/L |

FIG. 22C

| E. coli strain QC18 | | | | |
|---|---|---|---|---|
| Summary of changes by type | SNPs detail | | | |
| | Location (chromosome) | Gene(Description) | Nucleotide (reference/deviation) | Amino acid (old/new) |
| | | | | effect |
| SNP 10 | 1514315 | ydcC (Transposase IS4 family protein) | T/Y | SYNONYMOUS_CODING | I/I |
| MNP 0 | 1514876 | ydcC (Transposase IS4 family protein) | G/R | SYNONYMOUS_CODING | E/E |
| INS 0 | 239529 | ydfP (transposase IS4 family protein) | A/M | SYNONYMOUS_CODING | A/A |
| DEL 1 | 2845077 | rpoS (RNA polymerase sigma factor) | G/A | NON_SYNONYMOUS_CODING | T/I |
| MIXED 0 | 3531168 | malT (ATP-dependent transcriptional activator) | T/G | NON_SYNONYMOUS_CODING | V/G |
| Interval 0 | 3602338 | yhhI (Putative transposase) | A/R | NON_SYNONYMOUS_CODING | T/T or A |
| | 3603087 | yhhI (Putative transposase) | C/M | SYNONYMOUS_CODING | S/S |
| | 3603375 | yhhI (Putative transposase) | C/Y | SYNONYMOUS_CODING | D/D |
| | 3603387 | yhhI (Putative transposase) | G/S | SYNONYMOUS_CODING | L/L |
| | 727507 | ybfL (Predicted transposase, truncated) | G/R | SYNONYMOUS_CODING | G/G |

FIG. 22D

| E. coli strain QC19 Summary of changes by type | | E. coli strain QC19 SNPs detail | | | |
|---|---|---|---|---|---|
| | | Location (chromosome) | Gene (Description) | Nucleotide (reference / deviation) | effect | Amino acid (ref/new) |
| SNP | 11 | 1169320 | pntB (Adenylosuccinate lyase) | A/G | NON_SYNONYMOUS_CODING | V/A |
| MNP | 0 | 1514876 | ydcC (Transposase IS4 family protein) | G/R | SYNONYMOUS_CODING | E/E |
| INS | 0 | 233029 | yaiT (Transposase IS4 family protein) | A/M | SYNONYMOUS_CODING | A/A |
| DEL | 1 | 2845977 | rpoS (RNA polymerase sigma factor) | G/A | NON_SYNONYMOUS_CODING | T/I |
| MIXED | 0 | 3460098 | sfuA (Putative ABC transporter ATP-binding protein) | G/R | NON_SYNONYMOUS_CODING | C/C or F |
| Interval | 0 | 3531168 | malT (ATP-dependent transcriptional activator) | T/G | NON_SYNONYMOUS_CODING | V/G |
| | | 3602335 | yhhI (Putative transposase) | A/R | NON_SYNONYMOUS_CODING | I/T or A |
| | | 3603087 | yhhI (Putative transposase) | C/M | SYNONYMOUS_CODING | S/S |
| | | 3603375 | yhhI (Putative transposase) | C/Y | SYNONYMOUS_CODING | D/D |
| | | 3603387 | yhhI (Putative transposase) | G/S | SYNONYMOUS_CODING | L/L |
| | | 727597 | ybfL (Predicted transposase, truncated) | G/R | SYNONYMOUS_CODING | G/G |

FIG. 22E

| E. coli strain QC20 | | E. coli strain QC20 SNPs detail | | | |
|---|---|---|---|---|---|
| Summary of changes by type | | Location (chromosome) | Gene(Description) | Nucleotide (reference /deviation) | effect | Amino acid (old/new) |
| SNP | 9 | 1514876 | ydcC (Transposase IS4 family protein) | G/R | SYNONYMOUS_CODING | E/E |
| MNP | 0 | 239229 | yafF (Transposase IS4 family protein) | A/M | SYNONYMOUS_CODING | A/A |
| INS | 0 | 2845077 | rpoS (RNA polymerase sigma factor) | G/A | NON_SYNONYMOUS_CODING | T/I |
| DEL | 1 | 3531168 | malT (ATP-dependent transcriptional activator) | T/G | NON_SYNONYMOUS_CODING | V/G |
| MIXED | 0 | 3602338 | yhhI (Putative transposase) | A/R | NON_SYNONYMOUS_CODING | T/T or A |
| Interval | 0 | 3603087 | yhhI (Putative transposase) | C/M | SYNONYMOUS_CODING | S/S |
| | | 3603375 | yhhI (Putative transposase) | C/Y | SYNONYMOUS_CODING | D/D |
| | | 3603387 | yhhI (Putative transposase) | G/S | SYNONYMOUS_CODING | L/L |
| | | 727690 | ybfE (Predicted transposase, truncated) | T/W | SYNONYMOUS_CODING | L/L |

FIG. 22F

| E. coli strain QC21 | | | E. coli strain QC21 SNPs detail | | | |
|---|---|---|---|---|---|---|
| Summary of changes by type | | Location (chromosome) | Gene(Description) | Nucleotide (reference /deviation) | effect | Amino acid (old:new) |
| SNP | 9 | 239229 | yafF (Transposase IS4 family protein) | A/M | SYNONYMOUS_CODING | A/A |
| MNP | 0 | 2845977 | rpoS (RNA polymerase sigma factor) | G/A | NON_SYNONYMOUS_CODING | E/I |
| INS | 0 | 3531168 | malT (ATP-dependent transcriptional activation) | T/G | NON_SYNONYMOUS_CODING | V/G |
| DEL | 1 | 3602338 | ybhH (Putative transposase) | A/R | NON_SYNONYMOUS_CODING | T/T or A |
| MIXED | 0 | 3603087 | ybhH (Putative transposase) | C/M | SYNONYMOUS_CODING | S/S |
| Interval | 0 | 3603575 | ybhH (Putative transposase) | C/Y | SYNONYMOUS_CODING | D/D |
| | | 3603387 | ybhH (Putative transposase) | G/S | SYNONYMOUS_CODING | L/L |
| | | 7273607 | ybiL (Predicted transposase, truncated) | G/R | SYNONYMOUS_CODING | G/G |
| | | 7276990 | ybiL (Predicted transposase, truncated) | T/W | SYNONYMOUS_CODING | L/L |

FIG. 22G

E. coli strain QC22
SNPs detail

| E. coli strain QC22 Summary of changes by type | | Location (chromosome) | Gene(Description) | Nucleotide (reference/deviation) | effect | Amino acid (ref/new) |
|---|---|---|---|---|---|---|
| SNP | 11 | | | | | |
| MNP | 0 | 1169320 | purR (Adenylosuccinate lyase) | A/G | NON_SYNONYMOUS_CODING | V/A |
| INS | 0 | 1514876 | ydcC (Transposase IS4 family protein) | G/R | SYNONYMOUS_CODING | E/E |
| DEL | 1 | 239229 | yafF (Transposase IS4 family protein) | A/M | SYNONYMOUS_CODING | A/A |
| MIXED | 0 | 236259 | yafF (Transposase IS4 family protein) | T/Y | SYNONYMOUS_CODING | I/I |
| Interval | 0 | 2846077 | rpoS (RNA polymerase sigma factor) | G/A | NON_SYNONYMOUS_CODING | T/I |
| | | 3521168 | miaT (ATP-dependent transcriptional activator) | T/G | NON_SYNONYMOUS_CODING | V/G |
| | | 3602338 | yhhI (Putative transposase) | A/R | NON_SYNONYMOUS_CODING | T/T or A |
| | | 3603087 | yhhI (Putative transposase) | C/M | SYNONYMOUS_CODING | S/S |
| | | 3603375 | yhhI (Putative transposase) | C/Y | SYNONYMOUS_CODING | D/D |
| | | 3603387 | yhhI (Putative transposase) | G/S | SYNONYMOUS_CODING | L/L |
| | | 727587 | ykfL (Predicted transposase, truncated) | G/R | SYNONYMOUS_CODING | G/G |

FIG. 22H

*E. coli* strain QC23
SNPs detail

| *E. coli* strain QC23 Summary of changes by type | | Location (chromosome) | Gene( Description) | Nucleotide (reference /deviation) | effect | Amino acid (old/new) |
|---|---|---|---|---|---|---|
| SNP | 9 | 1514876 | ydcC (Transposase IS4 family protein) | G/R | SYNONYMOUS_CODING | E/E |
| MNP | 0 | 2843077 | rpoS (RNA polymerase sigma factor) | G/A | NON_SYNONYMOUS_CODING | T/I |
| INS | 0 | 3531168 | malT (ATP-dependent transcriptional activator) | T/G | NON_SYNONYMOUS_CODING | V/G |
| DEL | 1 | 3603338 | ybbI (Putative transposase) | A/R | NON_SYNONYMOUS_CODING | T/T or A |
| MIXED | 0 | 3603087 | ybbI (Putative transposase) | C/M | SYNONYMOUS_CODING | S/S |
| Interval | 0 | 3603375 | ybbI (Putative transposase) | C/Y | SYNONYMOUS_CODING | D/D |
| | | 3603387 | ybbI (Putative transposase) | G/S | SYNONYMOUS_CODING | L/L |
| | | 227507 | ybfL (Predicted transposase, truncated) | G/R | SYNONYMOUS_CODING | G/G |
| | | 727707 | ybfL (Predicted transposase, truncated) | C/Y | SYNONYMOUS_CODING | F/F |

FIG. 22I

| E. coli strain QC24 | | | | | |
|---|---|---|---|---|---|
| Summary of changes by type | | Gene(Description) | Nucleotide (reference abbreviation) | effect | Amino acid (old/new) |
| SNP | 11 | | | | |
| MNP | 0 | | | | |
| INS | 0 | | | | |
| DEL | 1 | | | | |
| MIXED | 0 | | | | |
| Interval | 0 | | | | |
| | | Location (chromosome) | | | |
| | | 1169320 purB (Adenylosuccinate lyase) | A/G | NON_SYNONYMOUS_CODING | V/A |
| | | 1514876 ydcC (Transposase IS4 family protein) | G/R | SYNONYMOUS_CODING | E/E |
| | | 258229 insT (Transposase IS1 family protein) | A/M | SYNONYMOUS_CODING | A/A |
| | | 2448077 rpoS (RNA polymerase sigma factor) | G/A | NON_SYNONYMOUS_CODING | T/I |
| | | 3331168 rssT (ATP-dependent transcriptional activator) | T/G | NON_SYNONYMOUS_CODING | V/G |
| | | 3662338 yhbJ (Putative transposase) | A/R | NON_SYNONYMOUS_CODING | V/I or A |
| | | 3663057 yhbL (Putative transposase) | C/M | SYNONYMOUS_CODING | S/S |
| | | 3663375 yhbL (Putative transposase) | C/Y | SYNONYMOUS_CODING | D/D |
| | | 3663557 yhbL (Putative transposase) | G/S | SYNONYMOUS_CODING | I/I |
| | | 727502 ybeL (Predicted transposase, truncated) | G/R | SYNONYMOUS_CODING | G/G |
| | | 727680 ybeL (Predicted transposase, truncated) | T/W | SYNONYMOUS_CODING | I/I |

FIG. 22J

| E. coli strain QC25 | | | | | |
|---|---|---|---|---|---|
| Summary of changes by type | | E. coli strain QC25 SNPs detail | | | |
| | | Location (chromosome) | Gene(Description) | Nucleotide (reference/deviation) | effect | Amino acid (old/new) |
| SNP | 10 | 1514876 | ydcC (Transposase IS4 family protein) | G/R | SYNONYMOUS_CODING | E/E |
| MNP | 0 | 239229 | yafF (Transposase IS4 family protein) | A/M | SYNONYMOUS_CODING | A/A |
| INS | 0 | 2845077 | rpoS (RNA polymerase sigma factor) | G/A | NON_SYNONYMOUS_CODING | T/I |
| DEL | 1 | 3331168 | malT (ATP-dependent transcriptional activator) | T/G | NON_SYNONYMOUS_CODING | V/G |
| MIXED | 0 | 3602338 | ybhJ (Putative transposase) | A/R | NON_SYNONYMOUS_CODING | T/T or A |
| Interval | 0 | 3603087 | ybhJ (Putative transposase) | C/M | SYNONYMOUS_CODING | S/S |
| | | 3603375 | ybhJ (Putative transposase) | C/Y | SYNONYMOUS_CODING | D/D |
| | | 3603387 | ybhJ (Putative transposase) | G/S | SYNONYMOUS_CODING | L/L |
| | | 727507 | ybfL (Predicted transposase, truncated) | G/R | SYNONYMOUS_CODING | G/G |
| | | 727702 | ybfL (Predicted transposase, truncated) | C/Y | SYNONYMOUS_CODING | F/F |

FIG. 22K

| E. coli strain QCTc26 Summary of changes by type | | Location (chromosome) | Gene(description) | Nucleotide (reference/deviation) | effect | Amino acid (ref/new) |
|---|---|---|---|---|---|---|
| SNP | 11 | 1514315 | ydaL (Transposase IS1 family protein) | T/Y | SYNONYMOUS_CODING | I/I |
| MNP | 0 | 1514876 | ykiC (Transposase IS4 family protein) | G/R | SYNONYMOUS_CODING | E/E |
| INS | 0 | 2292259 | yaiT (Transposase IS4 family protein) | A/M | SYNONYMOUS_CODING | A/A |
| DEL | 1 | 2845077 | rpoS (RNA polymerase sigma factor) | G/A | NON_SYNONYMOUS_CODING | T/I |
| MIXED | 0 | 3531168 | malT (ATP-dependent transcriptional activator) | T/G | NON_SYNONYMOUS_CODING | V/G |
| Interval | 0 | 3602338 | yhhI (Putative transposase) | A/R | NON_SYNONYMOUS_CODING | T/T or A |
| | | 3603887 | yjhI (Putative transposase) | C/M | SYNONYMOUS_CODING | S/S |
| | | 3603575 | yjhI (Putative transposase) | C/Y | SYNONYMOUS_CODING | D/D |
| | | 3603887 | yjhI (Putative transposase) | G/S | SYNONYMOUS_CODING | L/L |
| | | 4165528 | rpoC (DNA-directed RNA polymerase subunit beta') | A/C | NON_SYNONYMOUS_CODING | E/A |
| | | 727307 | ybfL (Predicted transposase, truncated) | G/R | SYNONYMOUS_CODING | G/G |

FIG. 22L

| E. coli strain QCTc27 Summary of changes by type | | E. coli strain QCTc27 SNPs detail | | | |
|---|---|---|---|---|---|
| | | Location (chromosome) | Gene(Description) | Nucleotide (reference/ alteration) | effect | Amino acid (old/new) |
| SNP | 11 | 1514576 | ydcC (Transposase IS4 family protein) | G/R | SYNONYMOUS_CODING | E/E |
| MNP | 0 | 2579172 | hisA (Phosphoribosylformimino-5-aminoimidazole carboxamide ribotide isomerase) | T/G | NON_SYNONYMOUS_CODING | V/G |
| INS | 0 | 2392229 | yaiT (Transposase IS4 family protein) | A/M | SYNONYMOUS_CODING | A/A |
| DEL | 1 | 2845077 | rpoS (RNA polymerase sigma factor) | G/A | NON_SYNONYMOUS_CODING | E/E |
| MIXED | 0 | 3331168 | malT (ATP-dependent transcriptional activator) | T/G | NON_SYNONYMOUS_CODING | V/G |
| Interval | 0 | 3603248 | yhhI (Putative transposase) | A/R | NON_SYNONYMOUS_CODING | T/T or A |
| | | 3603887 | yhhI (Putative transposase) | C/M | SYNONYMOUS_CODING | S/S |
| | | 3603375 | yhhI (Putative transposase) | C/Y | SYNONYMOUS_CODING | D/D |
| | | 3603387 | yhhI (Putative transposase) | G/S | SYNONYMOUS_CODING | L/L |
| | | 727507 | ybfL (Predicted transposase, truncated) | G/R | SYNONYMOUS_CODING | G/G |
| | | 727702 | ybfL (Predicted transposase, truncated) | C/Y | SYNONYMOUS_CODING | F/F |

FIG. 22M

E. coli strain QCTc28

SNPs detail

| E. coli strain QCTc28 Summary of changes by type | Location (chromosome) | Gene Description | Nucleotide (reference/deviation) | effect | Amino acid (old/new) |
|---|---|---|---|---|---|
| SNP 8 | 2845077 | rpoS (RNA polymerase sigma factor) | G/A | NON_SYNONYMOUS_CODING | T/I |
| MNP 0 | 3531168 | matT (ATP-dependent transcriptional activator) | T/G | NON_SYNONYMOUS_CODING | V/G |
| INS 0 | 3602338 | yhhI (Putative transposase) | A/K | NON_SYNONYMOUS_CODING | T/T or A |
| DEL 1 | 3603087 | yhhI (Putative transposase) | C/M | SYNONYMOUS_CODING | S/S |
| MIXED 0 | 3603375 | yhhI (Putative transposase) | C/Y | SYNONYMOUS_CODING | D/D |
| Interval 0 | 3603387 | yhhI (Putative transposase) | G/S | SYNONYMOUS_CODING | L/L |
| | 4165578 | rpoC (DNA-directed RNA polymerase subunit beta') | A/C | NON_SYNONYMOUS_CODING | E/A |
| | 727507 | ybfL (Predicted transposase, truncated) | G/R | SYNONYMOUS_CODING | G/G |

FIG. 22N

E. coli strain QCT429

SNPs detail

| E. coli strain QCT429 Summary of changes by type | | Location (chromosome) | Gene(Description) | Nucleotide (reference, deviation) | effect | Amino acid (alteration) |
|---|---|---|---|---|---|---|
| SNP | 10 | 239229 | yafF (Transposase IS4 family protein) | A/M | SYNONYMOUS_CODING | A/A |
| MNP | 0 | 2845077 | rpoS (RNA polymerase sigma factor) | G/A | NON_SYNONYMOUS_CODING | T/I |
| INS | 0 | 3531168 | malT (ATP-dependent transcriptional activator) | T/G | NON_SYNONYMOUS_CODING | V/G |
| DEL | 1 | 3625538 | yhhI (Putative transposase) | A/R | NON_SYNONYMOUS_CODING | T/T or A |
| MIXED | 0 | 3663087 | yhhI (Putative transposase) | C/M | SYNONYMOUS_CODING | S/S |
| Interval | 0 | 3663573 | yhhI (Putative transposase) | C/Y | SYNONYMOUS_CODING | D/D |
| | | 3663587 | yhhI (Putative transposase) | G/S | SYNONYMOUS_CODING | L/L |
| | | 4365578 | rpoC (DNA-directed RNA polymerase subunit beta') | A/C | NON_SYNONYMOUS_CODING | E/A |
| | | 722507 | ybfL (Predicted transposase, truncated) | G/R | SYNONYMOUS_CODING | G/G |
| | | 722690 | ybfL (Predicted transposase, truncated) | T/W | SYNONYMOUS_CODING | L/L |

FIG. 22O

| E. coli strain QCTc3B | | | | | |
|---|---|---|---|---|---|
| | | SNPs detail | | | |
| Summary of changes by type | Location (chromosome) | Gene(Description) | Nucleotide (reference deviation) | effect | Amino acid (old/new) |
| SNP 10 | 2389615 | nuoA (NADH dehydrogenase I subunit A) | A/M | SYNONYMOUS_CODING | G/G |
| MNP 0 | 29229 | yafP (Transposase IS4 family protein) | A/M | SYNONYMOUS_CODING | A/A |
| INS 0 | 2845077 | rpoS (RNA polymerase sigma factor) | G/A | NON_SYNONYMOUS_CODING | E/E |
| DEL 1 | 3521168 | malT (ATP-dependent transcriptional activator) | T/G | NON_SYNONYMOUS_CODING | V/G |
| MIXED 0 | 3602338 | ybbL (Putative transposase) | A/R | NON_SYNONYMOUS_CODING | E/T or A |
| Interval 0 | 3603087 | ybbL (Putative transposase) | C/M | SYNONYMOUS_CODING | S/S |
| | 3603375 | ybbL (Putative transposase) | C/Y | SYNONYMOUS_CODING | D/D |
| | 3603387 | ybbL (Putative transposase) | G/S | SYNONYMOUS_CODING | L/L |
| | 4165528 | rpoC (DNA-directed RNA polymerase subunit beta') | A/C | NON_SYNONYMOUS_CODING | E/A |
| | 727307 | ybfL (Predicted transposase, truncated) | G/R | SYNONYMOUS_CODING | G/G |

FIG. 22P

| E. coli strain QCTc31 | | | E. coli strain QCTc31 SNPs detail | | | |
|---|---|---|---|---|---|---|
| Summary of changes by type | | Location (chromosome) | Gene(Description) | Nucleotide (reference/ deviation) | effect | Amino acid (old/new) |
| SNP | 9 | 1514876 | ykfC (Transposase IS4 family protein) | G/R | SYNONYMOUS_CODING | E/E |
| MNP | 0 | 239259 | yafW (Transposase IS4 family protein) | A/M | SYNONYMOUS_CODING | A/A |
| INS | 0 | 2845077 | rpoS (RNA polymerase sigma factor) | G/A | NON_SYNONYMOUS_CODING | T/I |
| DEL | 1 | 3531168 | rnfT (ATP-dependent transcriptional activator) | T/G | NON_SYNONYMOUS_CODING | V/G |
| MIXED | 0 | 3602338 | ykiA (Putative transposase) | A/R | NON_SYNONYMOUS_CODING | T/T vs A |
| Interval | 0 | 3603487 | ykiA (Putative transposase) | C/M | SYNONYMOUS_CODING | S/S |
| | | 3603575 | ykiA (Putative transposase) | C/Y | SYNONYMOUS_CODING | D/D |
| | | 3603587 | ykiA (Putative transposase) | G/S | SYNONYMOUS_CODING | L/L |
| | | 4165578 | rpoC (DNA-directed RNA polymerase subunit beta') | A/C | NON_SYNONYMOUS_CODING | E/A |
| | | 727407 | ykfL (Predicted transposase, truncated) | G/R | SYNONYMOUS_CODING | G/G |
| | | 727600 | ykfL (Predicted transposase, truncated) | T/W | SYNONYMOUS_CODING | L/L |

FIG. 22Q

E. coli strain QCTc32
SNPs detail

| E. coli strain QCTc32 Summary of changes by type | Location (chromosome) | Gene(Description) | Nucleotide (reference/deviation) | effect | Amino acid (old/new) |
|---|---|---|---|---|---|
| SNP | | | | | |
| MNP 0 | | | | | |
| INS 0 | | | | | |
| DEL 1 | | | | | |
| MIXED 0 | | | | | |
| Interval 0 | | | | | |
| | 1514876 | ydcC (Transposase IS4 family protein) | G/R | SYNONYMOUS_CODING | E/E |
| | 2845077 | rpoS (RNA polymerase sigma factor) | G/A | NON_SYNONYMOUS_CODING | E/E |
| | 3531168 | malT (ATP-dependent transcriptional activator) | T/G | NON_SYNONYMOUS_CODING | V/G |
| | 3663338 | yhhI (Putative transposase) | A/R | NON_SYNONYMOUS_CODING | T/T or A |
| | 3663887 | yhhI (Putative transposase) | C/M | SYNONYMOUS_CODING | S/S |
| | 3663375 | yhhI (Putative transposase) | C/Y | SYNONYMOUS_CODING | D/D |
| | 4165978 | rpoC (DNA-directed RNA polymerase subunit beta') | A/C | SYNONYMOUS_CODING | L/L |
| | 727597 | yhL (Predicted transposase, truncated) | G/R | SYNONYMOUS_CODING | G/G |

FIG. 22R

| E. coli strain QCTc33 | | | | | |
|---|---|---|---|---|---|
| Summary of changes by type | | SNPs detail | | | |
| | | Location (chromosome) | Gene (Description) | Nucleotide (reference deviation) | effect | Amino acid (old/new) |
| SNP | 10 | 236228 | yafF (Transposase IS4 family protein) | A/M | SYNONYMOUS_CODING | A/A |
| MNP | 0 | 2445077 | rpoS (RNA polymerase sigma factor) | G/A | NON_SYNONYMOUS_CODING | T/I |
| INS | 0 | 3531168 | msfT (ATP-dependent transcriptional activator) | T/G | NON_SYNONYMOUS_CODING | V/G |
| DEL | 1 | 3603338 | ybbL (Putative transposase) | A/R | NON_SYNONYMOUS_CODING | T/T or A |
| MIXED | 0 | 3603087 | ybbL (Putative transposase) | C/M | SYNONYMOUS_CODING | S/S |
| Interval | 0 | 3603373 | ybbL (Putative transposase) | C/Y | SYNONYMOUS_CODING | D/D |
| | | 3603387 | ybbL (Putative transposase) | G/S | SYNONYMOUS_CODING | L/L |
| | | 4165878 | rpoC (DNA-directed RNA polymerase subunit beta') | A/C | NON_SYNONYMOUS_CODING | E/A |
| | | 727507 | ybhI (Predicted transposase, truncated) | G/R | SYNONYMOUS_CODING | G/G |
| | | 727782 | ybhI (Predicted transposase, truncated) | C/Y | SYNONYMOUS_CODING | F/F |

FIG. 22S

| E. coli strain QCT-c34 | | | E. coli strain QCT-c34 | | | |
|---|---|---|---|---|---|---|
| Summary of changes by type | | Location (chromosome) | Gene(Description) | Nucleotide (reference/deviation) | effect | Amino acid (old/new) |
| SNP | 10 | 1514315 | ydcC (Transposase IS4 family protein) | T/Y | SYNONYMOUS_CODING | I/I |
| MNP | 0 | 1514876 | ydcL (Transposase IS4 family protein) | G/R | SYNONYMOUS_CODING | E/E |
| INS | 0 | 2845077 | rpoS (RNA polymerase sigma factor) | G/A | NON_SYNONYMOUS_CODING | I/I |
| DEL | 1 | 3331168 | malT (ATP-dependent transcriptional activator) | T/G | NON_SYNONYMOUS_CODING | V/G |
| MIXED | 0 | 3603338 | yhhI (Putative transposase) | A/R | NON_SYNONYMOUS_CODING | T/T or A |
| Interval | 0 | 3603387 | yhhI (Putative transposase) | C/M | SYNONYMOUS_CODING | S/S |
| | | 3603375 | yhhI (Putative transposase) | C/Y | SYNONYMOUS_CODING | D/D |
| | | 3603387 | yhhI (Putative transposase) | G/S | SYNONYMOUS_CODING | L/L |
| | | 4165518 | rpoC (DNA-directed RNA polymerase subunit beta') | A/C | NON_SYNONYMOUS_CODING | E/A |
| | | 227397 | yhhI (Predicted transposase, truncated) | G/R | SYNONYMOUS_CODING | G/G |

FIG. 22T

| E. coli strain QCTc35 Summary of changes by type | | E. coli strain QCTc35 SNPs detail | | | | |
|---|---|---|---|---|---|---|
| | | Location (chromosome) | Gene(description) | Nucleotide (reference/deviation) | effect | Amino acid (old/new) |
| SNP | 10 | 1514876 | ydcC (Transposase IS4 family protein) | G/R | SYNONYMOUS_CODING | E/E |
| MNP | 0 | 220229 | yafB (Transposase IS4 family protein) | A/M | SYNONYMOUS_CODING | A/A |
| INS | 0 | 2845077 | rpoS (RNA polymerase sigma factor) | G/A | NON_SYNONYMOUS_CODING | L/L |
| DEL | 1 | 3306491 | gpcA (Transcription elongation factor) | T/C | NON_SYNONYMOUS_CODING | E/G |
| MIXED | 0 | 3531168 | malT (ATP-dependent transcriptional activator) | T/G | NON_SYNONYMOUS_CODING | V/G |
| Interval | 0 | 3603338 | yhhI (Putative transposase) | A/R | NON_SYNONYMOUS_CODING | I/I or A |
| | | 3603987 | yhhI (Putative transposase) | C/M | SYNONYMOUS_CODING | N/S |
| | | 3603375 | yhhI (Putative transposase) | C/Y | SYNONYMOUS_CODING | D/D |
| | | 3603387 | yhhI (Putative transposase) | G/S | SYNONYMOUS_CODING | L/L |
| | | 727507 | ybiL (Predicted transposase, truncated) | G/R | SYNONYMOUS_CODING | G/G |

FIG. 22U

BIOSYNTHESIS METHOD WITH HOST CELL AND QUALITY CONTROL SYSTEM

CROSS-REFERENCE TO RELATED APPLICATIONS

This application is a U.S. National Phase Application of PCT/US2016/050146, filed Sep. 2, 2016, which claims priority benefit of U.S. Provisional Patent Application Ser. No. 62/214,248, filed on Sep. 4, 2015, which is hereby incorporated by reference in its entirety.

STATEMENT REGARDING FEDERALLY SPONSORED RESEARCH & DEVELOPMENT

This invention was made with government support under grant number D13AP00038 awarded by the Defense Advanced Research Projects Agency; and grant numbers MCB1453147 and MCB1331194 awarded by the National Science Foundation. The government has certain rights in the invention.

BACKGROUND OF THE DISCLOSURE

The present disclosure relates generally to product biosynthesis, such as microbial production of chemicals, pharmaceuticals and fuels. More particularly, the present disclosure is directed to engineered microorganisms, methods, and systems for in vivo population quality control to improve overall biosynthetic product yield by continuously selecting for high-performing, non-genetic variants.

Biosynthesis from natural and engineered biosynthetic pathways enables bioproduction of many important chemicals from simple fuels (for example, ethanol, butanol and fatty acid derivatives) to intricate natural products (for example, artemisinin, strictosidine, and erythromycin). However, for bioproduction to be economically viable, biosynthetic performance often needs to be enhanced. Many creative approaches have been developed with varied success, including optimization of enzyme activities and expression levels, deletion of competing pathways, use of synthetic control systems or compartmentalization, and redesigning the central metabolism of the host. However, the effects of cell-to-cell variations in biosynthesis have been overlooked or altogether ignored with respect to bioproduction optimization. Non-genetic cell-to-cell variation is known to arise in isoclonal populations due to several naturally-inherent factors, including uneven cell division and cell cycles, variations in gene copy numbers, epigenetic modifications and micro-environments, and stochastic gene expression. These factors can generate a remarkable range of variation in protein and metabolite concentrations (regardless of plasmid-based or chromosome-based gene expression). These variations cause single-cell biosynthetic performance to vary significantly, giving rise to subpopulations of both low- and high-performing variants within isoclonal populations. This phenomenon may be undesirable in a bioproduction context, where subpopulations of low-performance variants may consume nutrients without efficiently synthesizing products, leading to suboptimal performance at the ensemble level.

Accordingly, there exists a need to improve overall biosynthetic performance. Given an effective mechanism for continuous enrichment of high-performance variants and elimination of low performers, non-genetic variation provides an avenue to enhance ensemble performance. Non-genetic cell-to-cell variation as an inherent characteristic of an isoclonal population can be broadly exploited to enhance biosynthetic performance. As described herein, a tool generally termed in vivo PopQC can exploit non-genetic variation for enhanced biosynthetic performance, for example by utilizing an intracellular product-responsive biosensor to regulate the expression of a selection gene, which continuously enriches high-performing, non-genetic variants under a given selection pressure.

SUMMARY OF THE DISCLOSURE

One aspect of the present disclosure describes a host cell comprising a product-responsive biosensor and a selection gene.

Another aspect of the present disclosure describes a method for product biosynthesis. The method comprises providing a host cell containing a PopQC construct. The PopQC construct includes at least a product-responsive biosensor and a selection gene. The method further comprises biosynthesizing the product using the host cell.

Yet another aspect of the present disclosure describes a quality control system for enhanced biosynthesis of a product. The system comprises a host cell containing a PopQC construct. The PopQC construct includes at least a product-responsive biosensor and a selection gene.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 1 is a listing of strains in accordance with the present disclosure.

FIGS. 2A and 2B depict binned mean pixel values from fluorescence microscopy in accordance with embodiments described herein.

FIG. 3 is a listing of plasmids in accordance with the present disclosure.

FIG. 4 is a listing of tyrosine-responsive boxes in accordance with the present disclosure.

FIGS. 7A-7C depict microscopy images of an engineered FFA-producing strain in accordance with the present disclosure.

FIG. 10 is a listing of supernatant target products in accordance with the present disclosure.

FIG. 12 depicts an illustration of biosynthetic performance and a biosynthetic pathway for FFA production in accordance with the present disclosure.

FIGS. 19A and 19B depict time-dependent conversion yield for a PopQC strain in accordance with the present disclosure.

FIGS. 21A and 21B depict FFA production and genome sequence of offspring colonies in accordance with the present disclosure.

FIGS. 22A-22U depict listings of strain sequence details in accordance with the present disclosure.

DETAILED DESCRIPTION OF THE DISCLOSURE

Figure 2A:
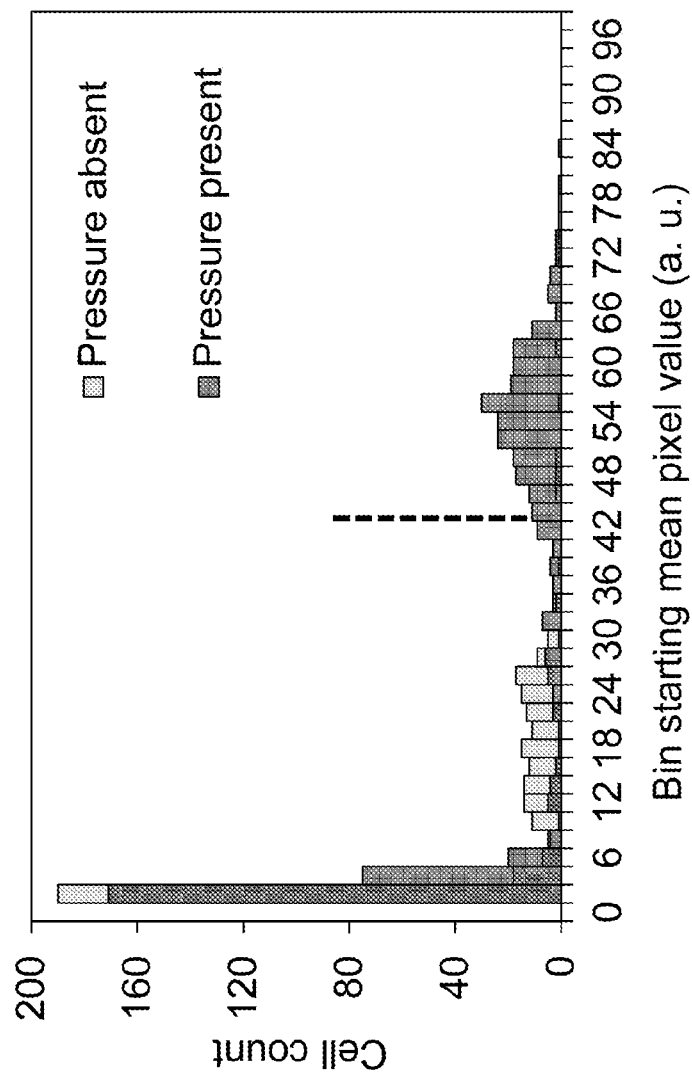

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

As used herein according to its ordinary meaning as understood by those skilled in the art, "promoter" refers to a polynucleotide sequence capable of initiating transcription of a DNA sequence in a cell.

As used herein, "a product-responsive transcription factor" refers to a transcription factor that binds to a product produced by a host cell. As understood by those skilled in the art, a transcription factor is capable of binding to a promoter and activating transcription upon binding of a product that induces a change in transcription factor conformation from an inactive to an active form, or upon binding of a product to the transcription factor itself. The transcription factor has DNA binding activity at "a product-responsive transcription factor binding site" in the vector such that the product-responsive transcription factor is capable of binding to the vector. While the product-responsive transcription factor is bound to the product-responsive transcription factor binding site, the promoter activity is repressed and no expression of the selection gene occurs. Upon binding of the product to the product-responsive transcription factor, the inhibition of the promoter activity is released and expression of the selection gene occurs.

As used herein, "activation of a promoter" refers to inducing expression of a gene that is operably linked to the promoter. The promoter is activated when a product-responsive transcription factor bound to the promoter binds a product such that gene expression can be initiated. Activation of a promoter can be determined relative to the level of gene expression when the transcription factor is bound to the product-responsive transcription factor binding site.

As used herein, "a selection gene" refers to a gene encoding a product essential for selection of higher-producing host cells. As discussed herein, an isoclonal or isogenic cell population can exhibit variation in a given culture medium, for example with respect to increased or decreased biosynthesis of a particular product. Consequently, low-producing cells may be characterized as having decreased cellular fitness, such that they can survive but exhibit little to no growth (i.e., they do not thrive). High-producing cells may be characterized as having increased cellular fitness, such that they are able to both survive and thrive. An applied selection pressure can be generally correlated with cell growth. Selection pressure may include, amendments made to the culture/growth medium (e.g., addition of an antibiotic or other substance), depletions made to the culture/growth medium (e.g., removal of a nutrient or other substance), and the like, as well as any other cell-growth and/or cell-survival related condition. For example, in some embodiments, the selection gene can be a survival gene such as an antibiotic resistance gene. Thus, when an antibiotic (i.e., a selection pressure) is included in the culture or growth medium, any host cell not expressing the selection (antibiotic resistance) gene fails to thrive (and in some cases fails, to survive) whereas any host cell expressing the selection (antibiotic resistance) gene will continue to grow. As another example, the selection gene can be a gene from an essential metabolic pathway for example. Thus, if the host cell is grown in a medium such as a minimal medium that lacks the essential metabolite (i.e., exposed to a selection pressure), expression of the gene from an essential metabolic pathway by the host cell results in the essential metabolite, resulting in selection of the host cell. In contrast, if the host cell lacks the ability to express the gene from an essential metabolic pathway, the host cell will have a decreased cellular fitness and will be unable to thrive (and in some cases, unable to survive) in the metabolite-depleted culture medium. In this way it is possible to both encourage high-producing cells and inhibit low-producing cells.

As used herein, "vector" and "expression vector" refer to a sequence(s) of nucleic acids to be expressed by the host cell and can include elements for insertion of nucleic acids to be expressed. Particular vectors include plasmids that include sequences for transcription of the nucleic acid sequence.

As used herein, "operably linked" refers to the functional linkage between two or more nucleic acid sequences such as a nucleic acid expression control sequence (such as promoters, enhancers, etc.) and a second nucleic acid sequence, where the nucleic acid expression control sequence directs transcription of the second nucleic acid sequence.

In one embodiment, the present disclosure is directed to a host cell. The host cell comprises a product-responsive biosensor and a selection gene. In some embodiments the product-responsive biosensor may be an intracellular product-responsive biosensor and may regulate expression of the selection gene (e.g., via a promoter). In some embodiments the product-responsive biosensor may be selected from a product-responsive transcription factor, a metabolite-based biosensor, an RNA-based biosensor, a protein-based biosensor, and a stress response-based biosensor. In some embodiments, the product-responsive biosensor and the selection gene may be incorporated into at least one vector of the host cell. In some embodiments, the product-responsive biosensor and the selection gene may be incorporated into a genome of the host cell. In some embodiments, the selection gene may be a survival gene and/or an essential metabolic pathway gene.

Host cells can include, for example, *Escherichia, Acinetobacter, Azotobacter, Bacillus, Bradyrizobium, Caulobacter, Chlamydia, Clostridium, Enterococcus, Klebsiella, Myxococcus, Planctomyces, Pseudomonas, Rhizobium, Rhodobacter, Salmonella, Sinorhizobium, Streptomyces, Rhodotorula, Lactococcus, Saccharomyces, Aspergillus, Yarrowia, Arabidopsis, Arachis, Vitis, Gossypium,* and *Vibrio* cells, as well as any other suitable prokaryotic or eukaryotic cells.

Biosynthesized products can include, for example, pharmaceuticals, fuels, proteins, fatty acids, high-molecular polymers, small molecular chemicals, industrial chemical precursors, other chemicals, and the like, and any other suitable biologically-produced chemical compound.

Any suitable product-responsive biosensor may be used. The product-responsive biosensor may be selected from a product-responsive transcription factor, a metabolite-based biosensor, an RNA-based biosensor, a protein-based biosensor, a protein activity-based biosensor, and a stress response-based biosensor. In some embodiments when the product-responsive biosensor is a product (or ligand) responsive transcription factor, it may be selected from a lipid-responsive transcription factor, an amino acid responsive transcription factor, a nucleic acid responsive transcription factor, a nucleic acid related compound responsive transcription factor, a carboyhdrate-responsive transcription factor, a central metabolite responsive transcription factor, a phenolic compound responsive transcription factor, a cofactor-responsive transcription factor, a metal ion responsive transcription factor, a steroid-responsive transcription factor, and the like, as well as other molecule responsive transcription factors known to those skilled in the art.

In some embodiments, the host cell may be a recombinant host cell. The recombinant host cell can include, for example, a first vector, a second vector, and a third vector. In some embodiments, the first vector may include a product-responsive transcription factor binding site, at least one promoter; and a selection gene (e.g., a heterologous selection gene), wherein the at least one promoter is operably linked to the selection gene. The first vector expression construct may contain other sequences necessary for expression of the selection gene. The second vector may include a nucleic acid encoding a product, wherein the product binds a product-responsive transcription factor and wherein the product-responsive transcription factor binds the product-responsive transcription factor binding site. The second vector recombinant nucleic acid can also comprise sequences sufficient for having the recombinant nucleic acid stably replicate in the host cell. The recombinant nucleic acid may be a replicon capable of stable maintenance in a host cell. In some embodiments, the replicon is a plasmid. The third vector may include a nucleic acid encoding a product, wherein the product binds a product-responsive transcription factor and wherein the product-responsive transcription factor binds the product-responsive transcription factor binding site.

Any suitable product-responsive transcription factor binding site known to those skilled in the art may be included in the first vector. The product-responsive transcription factor binding site is a nucleic acid sequence to which the product-responsive transcription factor is known to bind. In some embodiments, the product-responsive transcription factor that binds the product-responsive transcription factor binding site is naturally present in a host cell. In other embodiments, a host cell is engineered by introducing an expression cassette including a nucleic acid sequence encoding a product-responsive transcription factor into the host cell to express the product-responsive transcription factor. Examples of product-responsive transcription factor binding sites include FadR, TyrR, BenM, AlkS, XylR, CdaR, FapR, BadR, MarR, EmrR, CbaR, MetJ, GR, NagC, CynR, BmoR, NodD, MdcR, CatR, theophylline riboswitch, ammeline riboswitch, thiamine pyrophosphate riboswitch, AdoCbl riboswitch, and the like, and any other suitable product-responsive transcription factor binding sites known to those skilled in the art.

Suitable promoters may include any product-activated promoter (e.g., a FFA-activated promoter, a tyrosine-activated promoter) and the like, and other promoters known to those skilled in the art.

Suitable selection genes can include survival genes and essential metabolic pathway genes, and should be responsive to an associated selection pressure. In some embodiments, a selection gene may be a survival gene and can be an antibiotic resistance or sensitivity gene. Suitable antibiotic resistance or sensitivity genes are known to those skilled in the art and include, for example, a tetracycline resistance gene, an ampicillin resistance gene, a kanamycin resistance gene; a chloramphenicol resistance gene; a hygromycin resistance gene; a spectinomycin resistance gene; a gentamycin resistance gene; a erythromycin resistance gene; a streptomycin resistance gene and other antibiotic resistance genes known to those skilled in the art. In other embodiments, the selection gene can be a gene from an essential metabolic pathway. Genes from an essential metabolic pathway encode enzymes that are required by the host cell to metabolize a specific nutrient source which is required by the host cell in order to remain viable and for growth. A selection gene for an essential metabolic pathway may be selected from a biosynthetic operon associated with the metabolic pathway. Suitable amino acid biosynthetic pathway genes from essential metabolic pathways are known to those skilled in the art and include, for example, arginine, cysteine, glycine, glutamine, proline, tyrosine, alanine, aspartic acid, asparagine, glutamic acid, serine, phenylalanine, valine, threonine, tryptophan, methionine, leucine, isoleucine, lysine, and histidine. Use of a gene (or genes) from essential metabolic pathways is particularly advantageous it allows for avoiding the use of expensive and environmentally-problematic antibiotics. Any of the carbon sources metabolic pathways such as, for example, acetate, xylose, mannose, galactose, rhamnose, and arabinose are also suitable for use in some embodiments.

The second vector includes a nucleic acid encoding a product-responsive transcription factor. The second vector expression construct may contain other sequences necessary for expression of the product-responsive transcription factor. The recombinant nucleic acid can also comprise sequences sufficient for having the nucleic acid stably replicate in the host cell. The nucleic acid can be replicon capable of stable maintenance in a host cell. In some embodiments, the replicon is a plasmid.

The third vector includes a nucleic acid encoding a product, wherein the product binds a product-responsive transcription factor and wherein the product-responsive transcription factor binds the product-responsive transcription factor binding site. Any product produced using recombinant technology is suitable. The product can bind to the product-responsive transcription factor. The third vector expression construct may contain other sequences necessary for expression of a product. In some embodiments, the promoter sequence that directs expression of the product is an inducible promoter. In some embodiments, the promoter is a constitutive promoter. The recombinant nucleic acid can also include sequences sufficient for having the recombinant nucleic acid stably replicate in the host cell. The recombinant nucleic acid can be replicon capable of stable maintenance in a host cell. In some embodiments, the replicon is a plasmid.

In some embodiments, the product-responsive transcription factor blocks expression of the selection gene while bound to the product-responsive transcription factor binding site of the first vector.

Methods for introducing the recombinant vectors into suitable hosts are known to those of skill in the art and can include the use of $CaCl_2$ or other agents, such as divalent cations, lipofection, dimethyl sulfoxide (DMSO), protoplast transformation, conjugation, and electroporation.

In another embodiment, the present disclosure is directed to a method for product biosynthesis. The method includes providing a host cell containing a PopQC construct and biosynthesizing the product using the host cell. The PopQC construct includes at least a product-responsive biosensor and a selection gene. In some embodiments the product-responsive biosensor may regulate expression of the selection gene. In some embodiments the selection gene may be a survival gene and the method may further include applying a selection pressure comprising adding an antibiotic to the growth medium. In some embodiments the selection gene may be an essential metabolic pathway gene and the method may further include applying a selection pressure comprising depleting the growth medium of at least one essential nutrient. In some embodiments the product-responsive biosensor may be selected from a metabolite-based biosensor, an RNA-based biosensor, a protein-based biosensor, and a stress response-based biosensor.

In some embodiments, the method may be a method for selecting high-producing transformed host cells, such as for enhancing microbial fermentation efficiency by sensing product titer and controlling selection gene expression. In some embodiments, the method includes providing a transformed host cell (e.g., a recombinant host cell) and culturing the transformed host cell under selection pressure. The recombinant host cell includes a first vector, a second vector, and a third vector. The first vector may include a product-responsive transcription factor binding site, at least one promoter; and a selection gene (e.g., a heterologous survival gene), wherein the at least one promoter is operably linked to the selection gene. The second vector may include a nucleic acid encoding a product-responsive transcription factor. The third vector may include a nucleic acid encoding a product, wherein the product binds the product-responsive transcription factor and wherein the product-responsive transcription factor binds the product-responsive transcription factor binding site. In some embodiments, under the selection pressure the transformed host cell expresses the product and the product-responsive transcription factor, the product binds the product-responsive transcription factor, the product-responsive transcription factor binds the product-responsive transcription factor binding site, and the at least one promoter is activated by the product-responsive transcription factor to express a gene product, wherein the gene product causes the transformed host cell to become resistant to a compound or to produce a metabolite necessary to thrive or survive. Accordingly, increased production of the gene product further increases cellular fitness of the host cell.

Product produced by the recombinant host cells binds to the product-responsive transcription factor resulting in the activation of the promoter that controls expression of the selection gene. For cells producing low product levels, the selection gene is not sufficiently expressed and low-producing cells do not thrive, and in some embodiments cannot continue to grow. For cells producing high product levels, the product binds to the transcription factor to result in activation of the promoter controlling expression of the selection gene. Thus, for cells producing high product levels, the selection gene is expressed allowing high-product producing cells to rapidly grow. The method results in enhancing microbial fermentation efficiency because only high product producing cells are able to express the selection gene, thus synthesizing additional product.

A single colony can be used to inoculate a growth medium and are induced to begin product production. The cells making up the inoculation colony can be for example, any host cell described herein as well as other host cells known to those skilled in the art. In some embodiments, cells can be induced at the time of inoculation. In other embodiments, cells are induced after reaching an appropriate $OD_{600}$. In some embodiments for production under antibiotic selection pressure, an antibiotic is added to the growth medium at an appropriate final concentration. Antibiotic can be added prior to induction or following induction. In other embodiments, such as for production under the metabolic pathway selection pressure, a nutrient is depleted from the medium.

Any suitable product-responsive biosensor may be used, as described herein. The product-responsive biosensor may be selected from a product-responsive transcription factor, a metabolite-based biosensor, an RNA-based biosensor, a protein-based biosensor, a protein activity-based biosensor, and a stress response-based biosensor. In some embodiments when the product-responsive biosensor is a product (or ligand) responsive transcription factor, it may be selected from a lipid-responsive transcription factor, an amino acid responsive transcription factor, a nucleic acid responsive transcription factor, a nucleic acid related compound responsive transcription factor, a carboyhdrate-responsive transcription factor, a central metabolite responsive transcription factor, a phenolic compound responsive transcription factor, a cofactor-responsive transcription factor, a metal ion responsive transcription factor, a steroid-responsive transcription factor, and the like, as well as other molecule responsive transcription factors known to those skilled in the art.

Any suitable product-responsive transcription factor binding site known to those skilled in the art is included in the first vector as described herein.

Suitable selection genes should be responsive to an associated selection pressure as described herein. In some embodiments, the selection gene may be selected from, for example, an antibiotic resistance, sensitivity gene, and an essential metabolic pathway gene as described herein.

In yet another embodiment, the present disclosure is directed to a quality control system for enhanced biosynthesis of a product. The system includes a host cell containing a PopQC construct. The PopQC construct includes at least a product-responsive biosensor and a selection gene. In some embodiments the product-responsive biosensor may regulate expression of the selection gene under an applied selection pressure. In some embodiments the applied selection pressure may be selected from a nutrient-depleted cell growth medium and an antibiotic-amended cell growth medium. In some embodiments the product-responsive biosensor may be selected from a metabolite-based biosensor, an RNA-based biosensor, a protein-based biosensor, and a stress response-based biosensor. In some embodiments the selection gene may be selected from a survival gene and an essential metabolic pathway gene.

In some embodiments, the quality control system is a system for selecting high-producing host cells by sensing product titer and controlling selection gene expression. In some embodiments the system includes a host cell (e.g., a recombinant host cell) having a first vector, a second vector, and a third vector. The first vector includes a product-responsive transcription factor binding site, at least one promoter, and a selection gene (e.g. a heterologous selection gene), wherein the at least one promoter is operably linked to the selection gene. The second vector includes a nucleic acid encoding a product-responsive transcription factor. The third vector includes a nucleic acid encoding a product, wherein the product binds a product-responsive transcription factor and wherein the product-responsive transcription factor binds the product-responsive transcription factor binding site.

The product produced binds to the product-responsive transcription factor to result in activation of the promoter controlling expression of the selection gene. As a result of activation of the promoter, the selection gene is expressed allowing high-product producing cells to rapidly grow under culture conditions in which selection pressure is applied. The quality control system results in the selection of high-producing cells.

A single colony can be used to inoculate a growth medium and can be induced to begin product production. The cells making up the inoculation colony can be for example, any host cell described herein as well as other host cells known to those skilled in the art. In some embodiments, cells can be induced at the time of inoculation. In other embodiments, cells are induced after reaching an appropriate parameter level (e.g., an $OD_{600}$ level). In one embodiment, for production under the antibiotic selection pressure, an antibiotic may be added to the growth medium at an appropriate final concentration. Antibiotic may be added prior to induction or following induction. In another embodiment, for production under the metabolic pathway selection pressure, a nutrient may be depleted from the medium.

Any suitable product-responsive biosensor may be used, as described herein. The product-responsive biosensor may be selected from a product-responsive transcription factor, a metabolite-based biosensor, an RNA-based biosensor, a protein-based biosensor, a protein activity-based biosensor, and a stress response-based biosensor. In some embodiments when the product-responsive biosensor is a product (or ligand) responsive transcription factor, it may be selected from a lipid-responsive transcription factor, an amino acid responsive transcription factor, a nucleic acid responsive transcription factor, a nucleic acid related compound responsive transcription factor, a carbohydrate-responsive transcription factor, a central metabolite responsive transcription factor, a phenolic compound responsive transcription factor, a cofactor-responsive transcription factor, a metal ion responsive transcription factor, a steroid-responsive transcription factor, and the like, as well as other molecule responsive transcription factors known to those skilled in the art.

Any suitable product-responsive transcription factor binding site known to those skilled in the art is included in the first vector as described herein.

Suitable selection genes are known to those skilled in the art and should be responsive to an associated selection pressure as described herein. In some embodiments, the selection gene may be selected from a survival gene, an antibiotic resistance, a sensitivity gene, and an essential metabolic pathway gene as described herein.

The host cells and methods described herein provide a system to positively correlate product titer with cell fitness and thereby select for high-performing cells which then dominate the population. The system, termed in vivo population quality control (PopQC), contains at least one sensor-regulator (e.g., a product-responsive biosensor) and at least one selection gene. In some embodiments, the sensor-regulator or biosensor is a transcription factor (TF) whose DNA-binding activity is regulated by the product produced by the cell. Some embodiments include a promoter (e.g., a synthetic promoter) that is repressed by a transcription factor that binds to a transcription factor binding site in the vector. The product-activated sensor-regulator can provide tight control of gene expression via the promoter. The biosensor effectively and continuously monitors product titer and correspondingly regulates the selection genes in each cell, thus providing a growth advantage to high-performing cells via a mechanism to overcome a given selection pressure.

Techniques

Plasmids, Strains, and Culture Conditions.

All plasmids were constructed using BglBrick or Golden-Gate assembly methods, following well-established protocols. For cell cultures, single colonies were used to inoculate 5 mL of Luria-Bertani (LB) medium containing proper antibiotics (50 mg/L ampicillin, 50 mg/L kanamycin, and/or 30 mg/L chloramphenicol) and incubated at 37° C. with orbital shaking at 250 rpm. Overnight cultures were used to inoculate different media as described in each section. Minimal glucose medium was prepared by supplementing M9 salt (Sigma Aldrich) with 20 g/L glucose, 75 mM MOPS (pH 7.4), 2 mM $MgSO_4$, 0.1 mM $CaCl_2$, 3.8 µM thiamine, 10 µM $FeSO_4$, and micro-nutrients (3 µM $(NH_4)_6Mo_7O_{24}.4H_2O$, 400 µM boric acid, 30 µM $CoCl_2.6H_2O$, 15 µM $CuSO_4$, 80 µM $MnCl_2.4H_2O$ and 10 µM $ZnSO_4.7H_2O$). Leucine (40 mg/L) was added to cultures of DH10B in the minimal glucose medium, unless otherwise noted. Cell density ($OD_{600}$) was measured using a Cary 60 UV-Vis spectrophotometer (Agilent). Cell culture fluorescence was recorded on a TECAN Infinite F200PRO plate reader with an excitation wavelength of 535±9 nm and an emission wavelength of 620±20 nm for RFP fluorescence. The cell culture fluorescence was normalized by cell density. When cell cultures were incubated in a 96-well plate (150 µL for each well) inside the plate reader (218 rpm, 37° C.), culture fluorescence and OD were recorded every 1000 seconds.

FFA Production.

Overnight cultures in the minimal glucose medium were used to inoculate fresh minimal glucose medium with an initial $OD_{600}$ of 0.08. Cells were induced with 1 mM IPTG when $OD_{600}$ reached 0.6. For production under the pressure of Tc, Tc was added to a final concentration of 20 mg/L at 2.5 hours post-induction. For strains $QC_{FAL+}$ and $QC_{FAL-}$ (FIG. 1), overnight LB cultures were first washed with the minimal glucose medium to remove residual leucine. The washed cultures were then used to inoculate fresh minimal glucose medium containing varied amounts of leucine (ranging from 0 to 60 mg/L) with an initial $OD_{600}$ of 0.08. To overcome the growth limit in the absence of leucine, cells were induced with 1 mM IPTG for FFA production immediately following inoculation. All cultures were harvested after 3 days of production, unless otherwise noted. FFA (free fatty acid) titers in whole cell culture were quantified following previously published methods.

Fluorescence Microscopy.

Cells were vortexed thoroughly and washed twice in PBS. The washed cells were then stained for fluorescence imaging by adding Nile Red to the final PBS resuspension and incubating for over 5 min at room temperature. Stained cells were analyzed on an Axioskop 2 MOT microscope fitted with a 63x/1.40 oil objective (Zeiss). Phase contrast images were acquired first, followed immediately by fluorescence images at an excitation wavelength of 546 nm. Exposure times were identical for all images within each set of experiments. Eight-bit grey images were acquired with an AxioCam Cm1 and initially handled by the Axiovision 4.8 software suite (Zeiss). All image analysis was performed in ImageJ (National Institutes of Health). To quantify fluorescence intensity, all cells in phase contrast images were first traced and recorded as regions of interest (ROIs) in ImageJ. ROIs were then overlaid on corresponding, unedited raw fluorescence images and the mean grey value within each ROI was measured and recorded. The mean grey value is the sum of each pixel's grey value (from 0-255), divided by the total number of pixels. Three images were analyzed in this manner for strain $QC_{FAT+G}$ both with and without Tc treatment, for a total of 382 cells without Tc treatment and 550 cells with Tc treatment. An arbitrary mean grey value of 50 was chosen as the cutoff for "strong" fluorescence, and the proportion of cells with a mean grey value above 50 was divided by the total number of cells to give the proportion of cells exhibiting strong fluorescence (see FIGS. 2A and 2B). In particular, FIG. 2A illustrates binned mean pixel values for FFA-producing cells, while FIG. 2B illustrates binned mean pixel values for tyrosine producing cells. Automatic brightness and contrast was applied to phase contrast images, while identical min/max cutoff values (5 min/110 max) were applied to all fluorescence images to minimize the appearance of background fluorescence. Additionally, the ImageJ red lookup table was applied to all fluorescence images to simulate Nile Red fluorescence.

Quantification of Cell-to-Cell Variation in FFA Production.

Strain TES (FIG. 1) was cultivated for FFA production following the above-described procedure, except that uniformly $^{13}C$-glucose (all six carbons are labeled, Sigma Aldrich) was used as the sole carbon source to remove the effect of contaminant FFA from containers and solvents. After 20 hours of incubation under FFA production conditions, cells were collected, washed by filtered PBS, and stained by Nile Red. A small fraction of the stained cells was used for fluorescence imaging. The remaining cells were subjected to cell sorting using a BD FACSAriaII cell sorter equipped with a 488 nm laser for excitation and a 575±26 nm filter for detection. The threshold was set on side scatter. Forward scatter and side scatter were in logarithmic amplification, and a gate set on forward scatter versus side scatter was applied for cell collection. Cells were sorted into four bins according to their fluorescence intensities. More than 2.2 million cells were collected in each bin to ensure accurate FFA quantification.

The collected cells were concentrated using a nylon membrane (GNWP, 0.2 μm, 25 mm, EMD Millipore) to 1 mL and acidified with 100 μL of concentrated HCl. Undecanoic acid ($C_{11:0}$, 20 ng) was added as an internal standard. Total FFA were then extracted and derivatized to pentafluorobenzyl (PFB)-FFA for accurate quantification of low abundance FFA. Briefly, FFA was extracted with 1 mL of ethyl acetate three times and then the solvent was removed using an evaporator (Buchi). Next, 40 μL of solution consisting of N,N-dimethylacetamide, tetramethylammonium hydroxide, and methanol (1.0:0.5:1.5, w/w/w) was added to the dried extract and vortexed for 30 seconds. Another 40 μL of solution consisting of pentafluorobenzyl bromide and N,N-dimethylacetamide (1:3, v/v) was then added and vortexed thoroughly. After incubation at room temperature for over 15 min, the sample was transferred to a vacuum to remove all volatile solvents. The dried sample was added to 100 μL of water and extracted twice by 100 μL of methylene chloride. The solvent extract was then transferred into a GC vial and dried under vacuum conditions. Finally, the sample was re-suspended in 0.5 mL of heptane and analyzed using an Agilent model 7200 Accurate-Mass Q-TOF gas chromatography mass spectrometry (GC-Q-TOF, <5 ppm).

GC-Q-TOF was equipped with an Agilent 7890A GC with a Q-TOF analyzer capable of 15K resolving power, and a DB-5MS-UI low bleed column (30 m×0.25 mm×0.25 μm, Agilent J&W). Helium was used as a carrying gas at a flow rate of 1 mL/min. For each run, the column was equilibrated at 80° C. for 2 min, followed by a ramp to 300° C. at 18° C./min, and was held at 300° C. for 6 min. Q-TOF was run with a chemical ionization source operating in negative ion mode, whereby thermal electrons were generated by using methane as a buffer gas. Various split ratios, varying from none to 300:1, were programmed as necessary for sample concentration. $^{13}C$-labeled PFB-FFA were detected by their M-PFB (M-181) ions at characteristic retention times and m/z (C12:0, 12.829 min, m/z 211.2100; C14:1, 13.770 min, m/z 239.2324; C14:0, 13.862 min, m/z 241.2480; C16:1, 14.766 min, m/z 269.2704; C16:0, 14.848 min, m/z 271.2860; C18:1, 15.867 min, m/z 299.3084; C18:0, 15.953 min, m/z 301.3240). The samples were quantified using both internal and external standards (2-1000 ng/mL).

Characterization of FFA PopQC.

The FFA biosensor plasmid pBARk-rfp contains a FFA-activated $P_{AR}$ promoter 5' of a red fluorescent protein (rfp) gene. $P_{AR}$ was replaced by the promoters $P_{AR1}$, $P_{AR2}$, and $P_{AR3}$ (which do not respond to FFA) in plasmids pBAR1k-rfp, pBAR2k-rfp, and pBAR3k-rfp, respectively. The FFA biosensor and its controls were evaluated following known methods. Hill equation was used for data fitting.

For PopQC constructs, a tetracycline resistance gene tetA, encoding a Tc efflux system, or a leucine operon leuABCD, encoding genes in leucine biosynthesis, was inserted 3' of the promoter $P_{AR}$. To evaluate the responses of PopQC (with tetA) to exogenous oleic acid in the presence of Tc, strain $QC_{FAT}$ (FIG. 1) was first grown in a minimal glucose medium with 0.5% tergitol to exponential phase. Cells were then used to inoculate fresh minimal media containing varied amounts of oleic acid (2-1000 μM). Cells were incubated in a 96-well plate inside the plate reader. Tc was added to a final concentration of 20 mg/L at 2.5 hours post incubation. Specific growth rates at the exponential cell growth phase (~5 hours after inoculation) were calculated from monitored cell density ($OD_{600}$).

Glucose Analysis.

Glucose concentration was determined by high-performance liquid chromatography (HPLC) following Waters standard protocols. Briefly, filtered culture supernatants were analyzed by a Waters HPLC system including a Waters e2695 separation module, a Waters 2414 RID detector, and a Waters high performance carbohydrate column (P/N WAT044355). The separation was performed using an elution (20:80, water:acetonitrile) with 1.4 mL/min flow rate at room temperature.

Flow Cytometry.

$QC_{FAT+Q}$ cells were cultivated as described above and collected at different time points. Collected cells were washed with filtered PBS buffer followed by immediate treatment with 2 mg/mL of kanamycin to stop protein synthesis. Treated cells were kept on ice until use. Prior to flow cytometry analyses, samples were vortexed thoroughly. The analysis was performed using a BD LsrFortessa equipped with a laser (488 nm, 50 mW) and a filter (505LP, 530/30). Forward scatter and side scatter were in logarithmic amplification, and the threshold was set on side scatter. The data analysis and visualization were performed using FlowJo (Treestar). To ensure consistency, a gate set on forward scatter versus side scatter was applied for each plot.

Genome Sequencing.

The freshly transformed strain $QC_{FAT+}$ harboring PopQC (the parent strain) was first cultivated for FFA production in the absence or presence of Tc. Cell cultures at different time points during production were collected and spread onto LB agar plates with appropriate antibiotics to isolate offspring colonies. Both the parent strain (from glycerol stock, never cultivated under FFA production conditions) and offspring colonies (10 colonies isolated from either Tc-treated or untreated cultures after 72 hours incubation) were used for genome sequencing. Genomic DNAs were isolated using a genomic DNA purification kit (Thermo Scientific). The library was prepared following standard protocols, and the whole-genome sequencing was performed on an Illumina HiSeq. Reads were aligned to a DH1 strain reference genome (*Escherichia coli* dh1 asm27010v1 GCA_000270105.1.23, along with three engineered plasmids pE8a-fadR, pA5c-tesA, and pBARk-tetA/rfp, see FIG. 3) using Novoalign. SNPs were identified by SAMtools software and annotated by snpEFF software, and data were viewed and confirmed using IGV software.

Construction and Characterization of Tyrosine Sensors.

The TyrR (tyrosine-responsive TF) expressing plasmid pE8a-tyrR was constructed by inserting an *E. coli* tyrR 3' of $P_{BAD}$ in a BglBrick plasmid pE8a (colE1 origin, ampicillin resistance, $P_{BAD}$ promoter, araC). The strong and weak tyrosine boxes (FIG. 4) from tyrosine-regulated *E. coli* promoters were inserted upstream of a phage promoter, leading to the synthetic promoters $P_{T0}$, $P_{T1}$, and $P_{T2}$. These synthetic promoters were then cloned 5' of rfp, generating tyrosine biosensor plasmids pBT0k-rfp, pBT1k-rfp, and pBT2k-rfp, respectively. To evaluate responses of the tyrosine sensors to exogenous tyrosine, pE8a-tyrR was co-transformed with one of the biosensor plasmids to *E. coli* MG1655. Cells were cultivated at 37° C. in minimal glucose medium with varied amounts of tyrosine (ranging from 0 to 0.25 g/L). Culture fluorescence was recorded as described above.

PopQC for Enhancing Tyrosine Production.

A tyrosine-producing plasmid pA5c-tyr was constructed by placing a feedback-resistant aroG* (amplified from plasmid pS4) upstream of tyrB-tyrA*-aroC-aroA-aroL (from pY3) and cloning the whole gene cluster into a BglBrick plasmid pA5c (p15A origin, chloramphenicol resistant, $P_{LacUV5}$ promoter, lacI). Plasmids pBT0k-tetA-rfp, pBT1k-tetA-rfp and pBT2k-tetA-rfp were constructed by inserting tetA 5' of rfp in the tyrosine sensor plasmids pBT0k-rfp, pBT1k-rfp, and pBT2k-rfp, respectively. The PopQC-regulated tyrosine overproducing strains were then constructed by co-transforming the plasmids pA5c-tyr and pE8a-tyrR along with pBT1k-tetA-rfp or pBT2k-tetA-rfp, resulting in strains $QC_{TYT1+}$ and $QC_{TYT2+}$, respectively.

Tyrosine production was performed under the same culture condition and Tc treatment as described for FFA production. Tyrosine was quantified by adding 10 µL of concentrated HCl to 120 µL of cell culture and incubated at 55° C. for 30 min. Then 1 mL of water was added and mixed, followed by centrifugation at 12000 rpm for 10 min. The supernatant was analyzed for quantification using a Waters HPLC system (Waters e2695 separations module and Waters 2489 UV/visible detector, equipped with an Agilent Zorbax Eclipse XDB-C18 column, 3.5 µm, 2.1×50 mm). The separation was performed using a gradient elution of water (A) and methanol (B) (0-2 min, 1% of B; 2-4 min, 1% to 5% of B; 4-6 min, 5% to 40% of B; 6-7 min, 40% of B; 7-10 min, 40% to 1% of B; 10-25 min, 1% of B). The flow rate was 0.1 mL/min and the detection wavelength was set to 280 nm.

Model Description.

To simulate chemical production by strains with and without PopQC, a model was constructed in MATLAB (MathWorks) using FFA as the biosynthetic product. To prepare the model, the following steps were taken.

Step 1. FFA abundance in each single cell was denoted as X. A normal distribution function (denoted as p(x)) was used to describe the initial FFA distribution across the entire population before a selection pressure was applied:

$$X \sim N(X_{mean}, \tau^2) \quad (1)$$

where $X_{mean}$ is the mean FFA abundance before selection pressure was applied, and σ is the variation of FFA distribution.

To calculate FFA production, the entire population (denoted as Pop) was divided into numerous sub populations (denoted as $Pop_i$) with FFA abundance in each sub population falling into small, even intervals ($X_i$, $X_i+\Delta X$), where $\Delta X \to 0$, $i=1, 2, 3 \ldots m$, and m is the total number of sub populations.

Step 2. After a unit of elapsed time, $\Delta t$, the number of cells within $Pop_i$ was increased by $\Delta^1 n_i = \mu \cdot n_i \cdot \Delta t$, where $n_i$ is the number of cells in $Pop_i$ before $\Delta t$, µ is the specific growth rate, and the superscript indicates the number of $\Delta t$ passed. Thus the total number of cells in $Pop_i$ after one round of $\Delta t$ is:

$$^1n_i = n_i + \Delta^1 n_i \quad (2)$$

Next, $^1X_{i,mean}$, the mean FFA abundance in $^1Pop_i$ after $\Delta t$ was considered. $^1X_{i,mean}$ consists of FFA both endogenously produced during $\Delta t$ and inherited from the parent cells. Due to non-genetic variation, a parent cell with high productivity may divide into daughter cells that have either low or high productivity. Thus, to calculate endogenously produced FFA, an averaged productivity, $k_{FA}$, was used for all sub populations. Inherited FAs were set to be evenly distributed among all daughter cells within $Pop_i$ to calculate $^1X_{i,mean}$. Thus, the mean FFA abundance in $^1Pop_i$ is $$^1X_{i,mean} = k_{FA} \cdot \Delta t + \frac{\frac{2X_i + \Delta X}{2} \cdot n_i}{^1n_i} \quad (3)$$

where $k_{FA} \cdot \Delta t$ represents the endogenously produced FFA during $\Delta t$, and $$\frac{\frac{2X_i + \Delta X}{2} \cdot n_i}{{}^1 n_i}$$

represents the amount of FFA that $^1Pop_i$ inherits from $Pop_i$. A normal distribution with the same variation σ was applied to consider non-genetic variation for $^1Pop_i$. Therefore, the FFA abundance for cells in $^1Pop_i$ follows a normal distribution function $^1p_i(x)$, where $$^1X_i \cdot N(^1X_{i,mean}, \sigma^2), \quad (4)$$

Equations (2)-(4) were then combined to give, $$^1X_i \sim N\left(k_{FA} \cdot \Delta t + \frac{2X_i + \Delta X}{2 + 2\mu \cdot \Delta t}, \sigma^2\right) \quad (5)$$

Step 3. The FFA distribution function of the whole population after time $\Delta t$, $^1p(x)$, was then obtained by adding the probability distribution functions of each $^1Pop_i$, $$^1p(x) = \sum_{i=1}^{m} {}^1w_i \cdot {}^1p_i(x) \quad (6)$$

where $^1w_i$ is the weight of each $^1p_i(x)$, $$^1w_i = \frac{{}^1n_i}{\sum_{i=1}^{m} {}^1n_i} \quad (7)$$

Equations (6) and (7) were then combined to give, $$^1p(x) = \sum_{i=1}^{m} \frac{{}^1n_i}{\sum_{i=1}^{m} {}^1n_i} \cdot {}^1p_i(x) \quad (8)$$

The calculation was then performed numerically and the resulting distribution was used as the starting point for the next round of simulations.

Step 4. FA titer ($^1FA$) and the total number of cells ($^1n$) of $^1Pop$ is calculated by $$^1FA = \sum_{i=1}^{m} {}^1n_i \cdot \frac{2x_i + \Delta x}{2} \cdot c \quad (9)$$

$$^1n = \sum_{i=1}^{m} {}^1n_i \quad (10)$$

where c is a constant that converts FFA units to g/L.

Step 5. Step 2, Step 3 and Step 4 were repeated for many cycles to obtain a time course evolution of FFA distribution, FFA titer, and cell growth in the whole population ($^2Pop$, $^3Pop$ . . . ).

Figure 5:
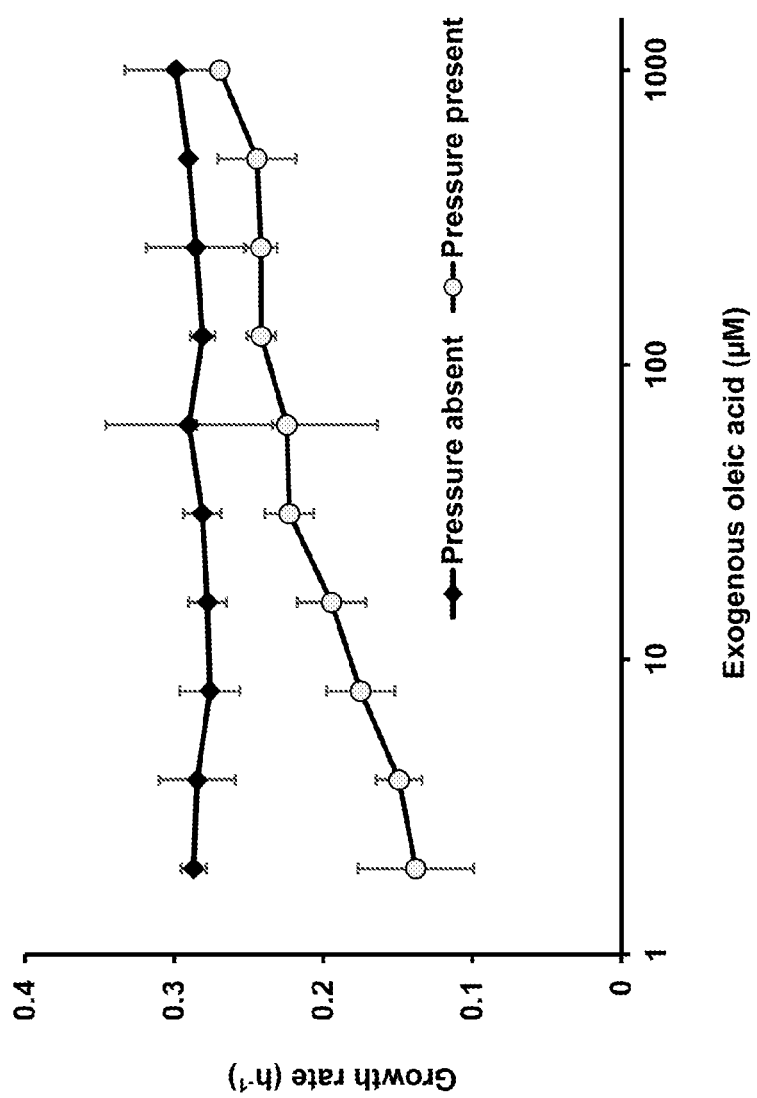
FIG. 5 depicts specific growth rate of engineered cells in accordance with the present disclosure.
Figure 6A:
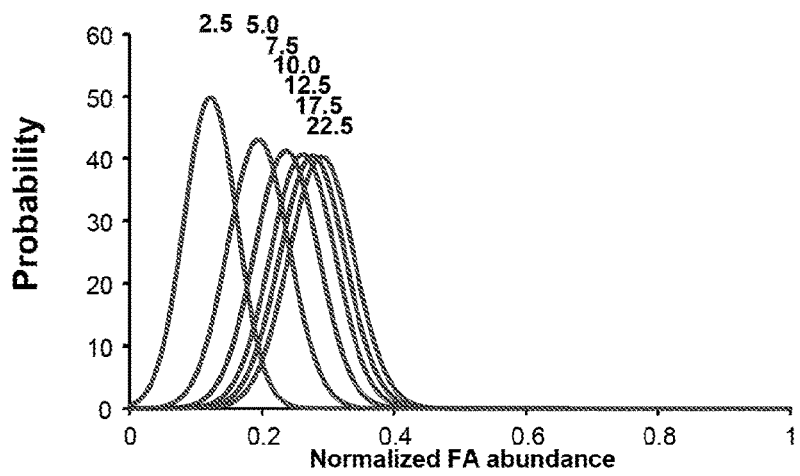
FIGS. 6A-6C depicts modeled FFA abundance distributions in accordance with the present disclosure.
Figure 6B:
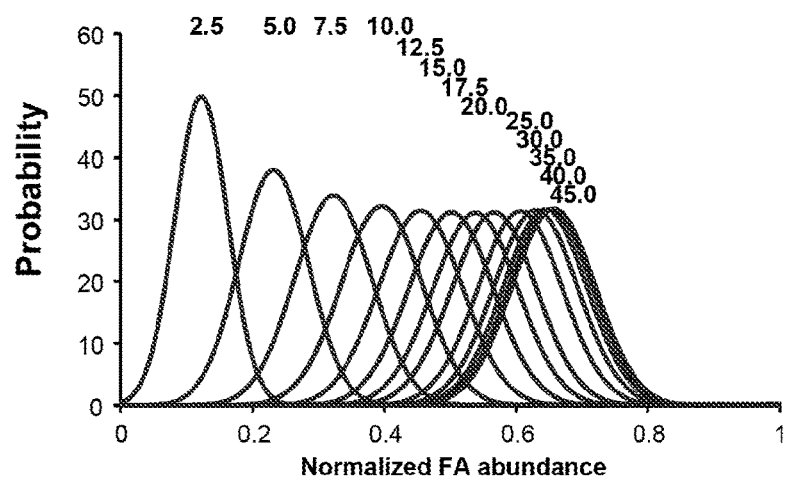
Figure 6C:
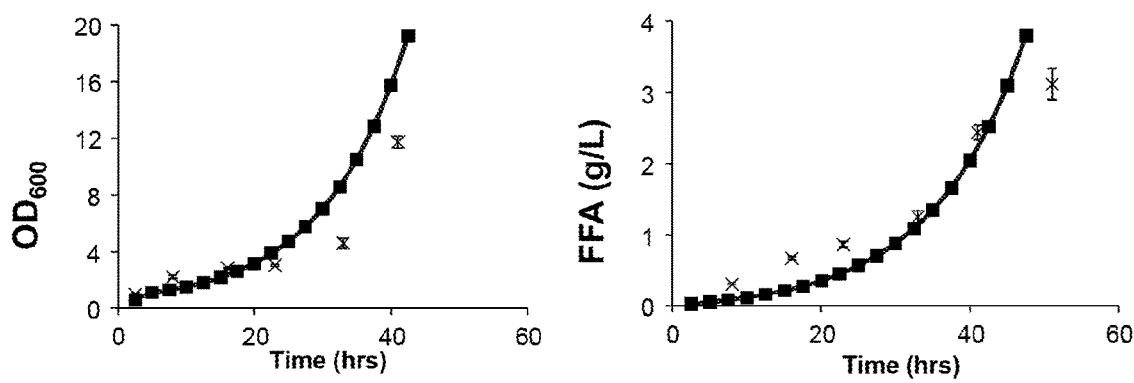

The model was parameterized by values obtained either from experimental data or from literature. Specifically, $X_{mean}$ was determined experimentally by dividing the FFA titer (after subtracting background FFA) by the total cell density at 2.5 hours post induction of the FFA pathway (when selection pressure was applied). The specific growth rate μ of cells treated with or without Tc was determined experimentally (FIG. 5). For strains without selection pressure, μ is a constant value. For strains cultivated under selection pressure, μ varies with intracellular FFA concentrations, which was simulated by fitting experimental data in FIG. 5 to a Hill equation ($\mu = Hilla \cdot x^{Hilln}/(Hillk^{Hilln} + x^{Hilln})$) to obtain the correlation of μ to FFA titer. A scaling factor (s) was used to correlate extracellular FFA to intracellular FFA. $k_{FA}$ was determined experimentally using ensemble FFA productivity. A broad range of values was tested in the simulation (σ=0.0001 to 0.01) with no effect on the resulting trends (i.e. relative FFA abundance and overall titer). FFA distributions from the PopQC strain with and without selection pressure at several time points are plotted in FIGS. 6A-6C. A model was formulated to describe the production and cell-to-cell variation of FFA under exponential growth phase. Time course of FFA abundance distributions in strains without (FIG. 6A) and with (FIG. 6B) PopQC selection are shown. Time points in the unit of hour are presented above peaks. FIG. 6C shows modeled cell growth (left) and overall FFA titer (right) under PopQC selection. Squares indicate simulated results, and crosses indicate experimental measurements. The parameters used are summarized in the table below.

TABLE 1

Parameters used in the simulation.

| Parameter | Value | Notes |
|---|---|---|
| $X_{mean}$ | 0.0244 (pg/cell) | Calculated value |
| σ | 0.008 (pg/cell) | σ is varied from 0.01 to 0.0001 |
| Δx | 0.0001 (pg/cell) | — |
| Δt | 2.5 (hours) | — |
| $k_{FA}$ | 0.00976 (g · L$^{-1}$ · h$^{-1}$) | Calculated value |
| Hilla | 0.2754 (h$^{-1}$) | Fitted value |
| Hilln | 0.4612 | Fitted value |
| Hillk | 0.0006277 (pg/cell) | Fitted value |
| μ (no selection pressure) | 0.28 (h$^{-1}$) | Calculated value |
| s | 1000 | — |
| c | 10$^{-9}$ | — |

EXAMPLES

Example 1

Figure 8:
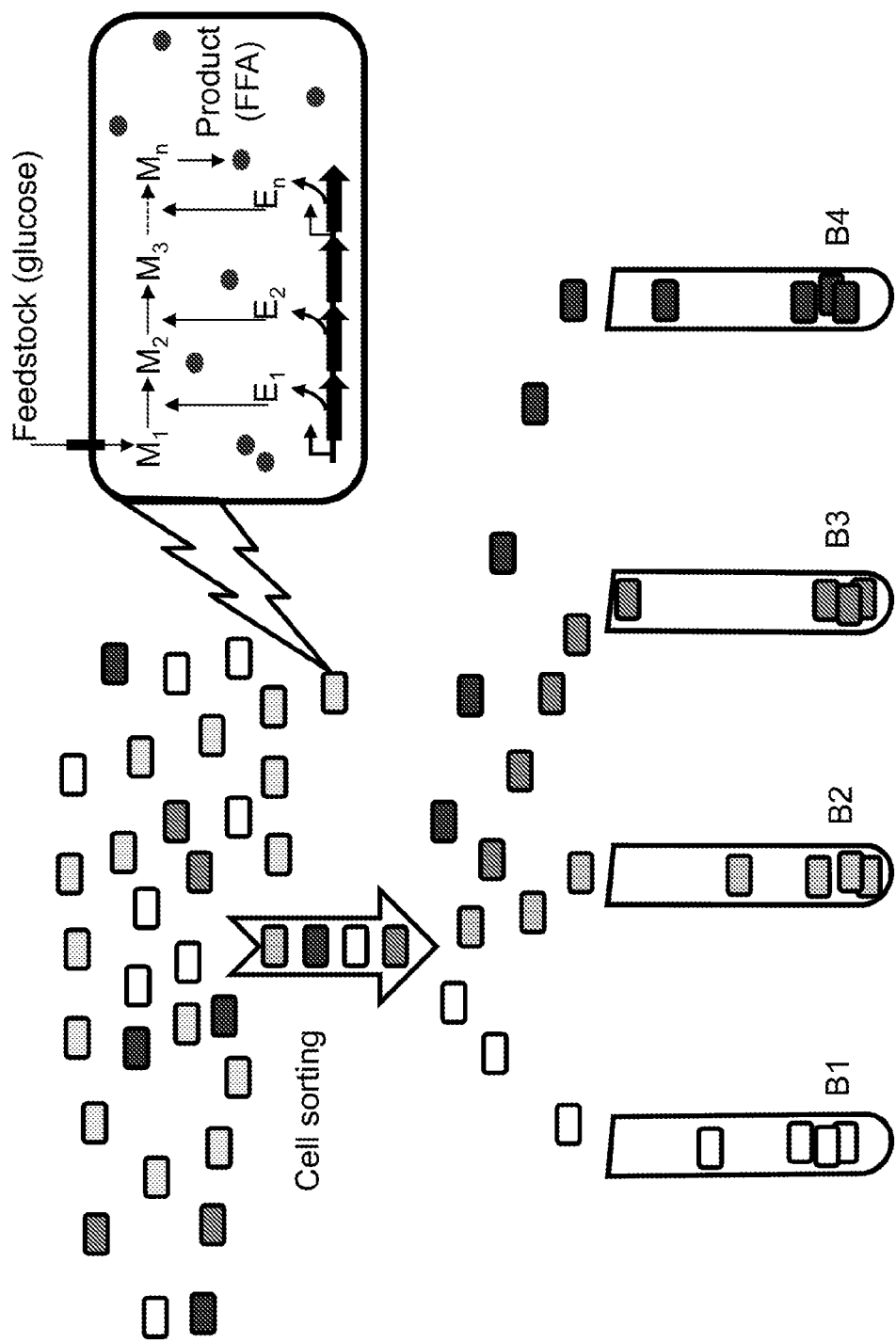
FIG. 8 depicts a schematic representation of non-genetic variants and cell sorting in accordance with the present disclosure.
Figure 9A:
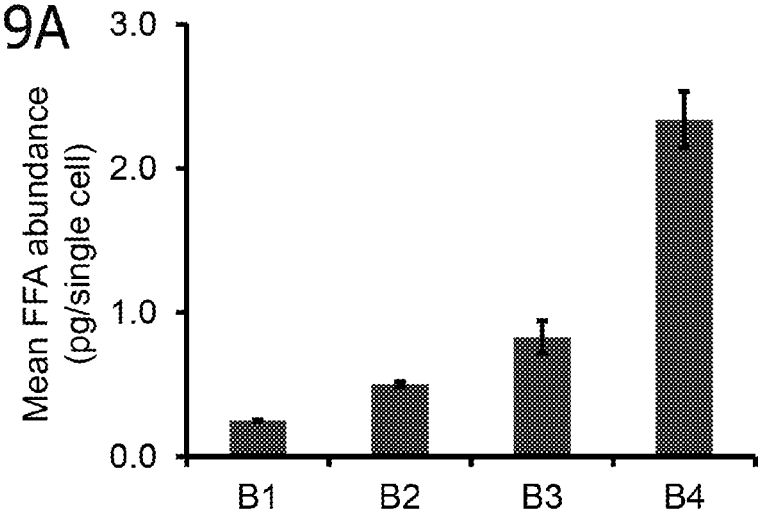
FIGS. 9A-9C depict bin-sorted data of an isoclonal population in accordance with the present disclosure.
Figure 9B:
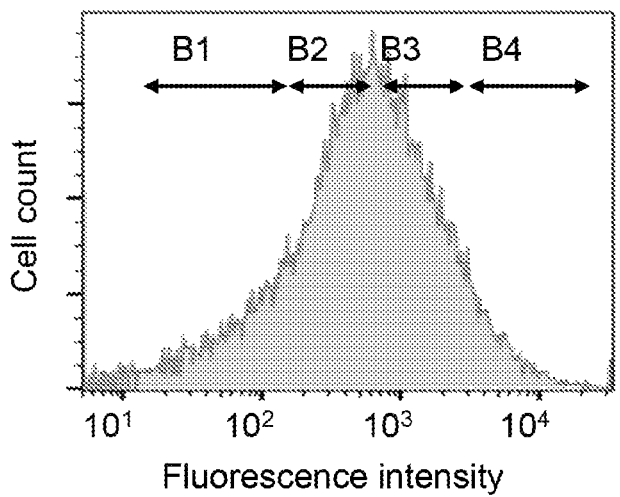
Figure 9C:
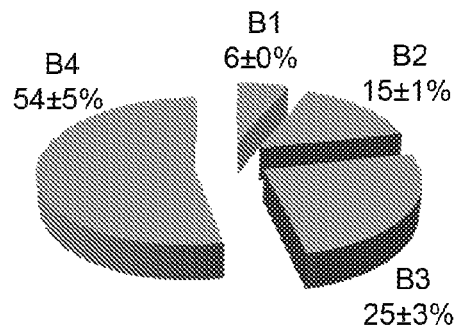

Quantification of biosynthetic heterogeneity of FFA product from an engineered FFA-overproducing *E. coli* strain. An analytical approach coupling Fluorescence-Activated Cell Sorting (FACS) with $^{13}$C-aided GC-MS was developed to confirm and precisely quantify biosynthetic heterogeneity of FFA product from an engineered FFA-overproducing *E. coli* strain TES (FIG. 1). Starting from a single colony, cultures were grown under typical fermentation conditions to produce FFA. Cells were collected and stained with a lipophilic dye, Nile Red. Marked heterogeneity of staining suggested significant cell-to-cell variation in FFA biosynthesis (FIGS. 7A-7C). FIGS. 7A-7C, FIG. 8, and FIGS. 9A-9C depict cell-to-cell variation in performance of the FFA pathway within an isoclonal population. FIGS. 7A-7C show an engineered FFA-producing *E. coli* strain (TES, see FIG. 1) cultivated in a glucose minimal medium for FFA production. The cells, stained by a lipophilic dye Nile Red (50 µg/L), were analyzed by fluorescence microscopy. Fluorescence (FIG. 7A), phase contrast (FIG. 7B), and phase contrast/fluorescence overlay (FIG. 7C) images are shown. FIG. 8 is a schematic representation of variants and cell sorting. The FFA biosynthetic pathway comprises multiple metabolites ($M_1$-$M_n$) and enzymes ($E_1$-$E_n$) encoded by both naturally-occurring and engineered genes. Within the isoclonal population, individual cells synthesized different amounts of FFA (lower FFA producing cells are shown lighter, higher producing cells are shown darker) and were subjected to sorting according to their product abundance. FIGS. 9A-9C illustrate the same pool of cells imaged in FIGS. 7A-7C as divided into four subpopulations (B1-B4). Distribution and gating of the population are shown in FIG. 9B. Mean FFA abundance for the cells in each bin was quantified using a high resolution GC-MS aided by $^{13}$C-labelling. FIG. 9C, Proportion of FFA produced by each subpopulation. To quantify the heterogeneity and confirm that it was not an artifact of staining or microscopy, FACS was used to separate the stained cells into four bins (>2.2 million cells each) according to fluorescence intensity (FIGS. 8 and 9B), and subsequently quantified FFA with high-resolution GC-MS. The mean FFA abundance for cells in each bin varied by as much as 9-fold (FIG. 9C). Notably, subpopulation B4—a minority (15%) of the total cells—produced more than half (54±5%) of the total FFA (FIG. 9C), demonstrating wide variation in biosynthetic performance. Throughout these experiments, extracellular FFA remained a negligible fraction (<2%) of the total produced FFA (FIG. 10). These results indicated the potential for improving ensemble bioproduction by increasing the proportion of high-performing variants. FIG. 10 is a table summarizing target products in the supernatant. Strains $QC_{FAT+}$ and $QC_{TYT1+}$ were used for FFA and tyrosine production, respectively. The strains were grown in minimal glucose medium without selection pressure. The supernatant was obtained through high speed centrifugation. Most of the tyrosine product was found in the culture supernatant (>80%), in contrast to the FFA product which accumulates in host cells, perhaps as a result of the exporter YddG, which has been found to promote tyrosine efflux. However, the presence of high concentration exogenous tyrosine should down-regulate the expression of tyrosine importers AroP and TyrP. With low expression of importers and a slow free diffusion of tyrosine, we reason that the intracellular tyrosine contents in tyrosine-producing strains would not average across the bulk population during the limited fermentation time. Thus, PopQC would still function well for tyrosine production. This conclusion is supported by the fact that a tyrosine biosensor-regulator, which down-regulates mutation rate in response to tyrosine concentration was successfully applied for genome engineering to acquire high production mutants from a bulk cell population.

Example 2

Figure 11:
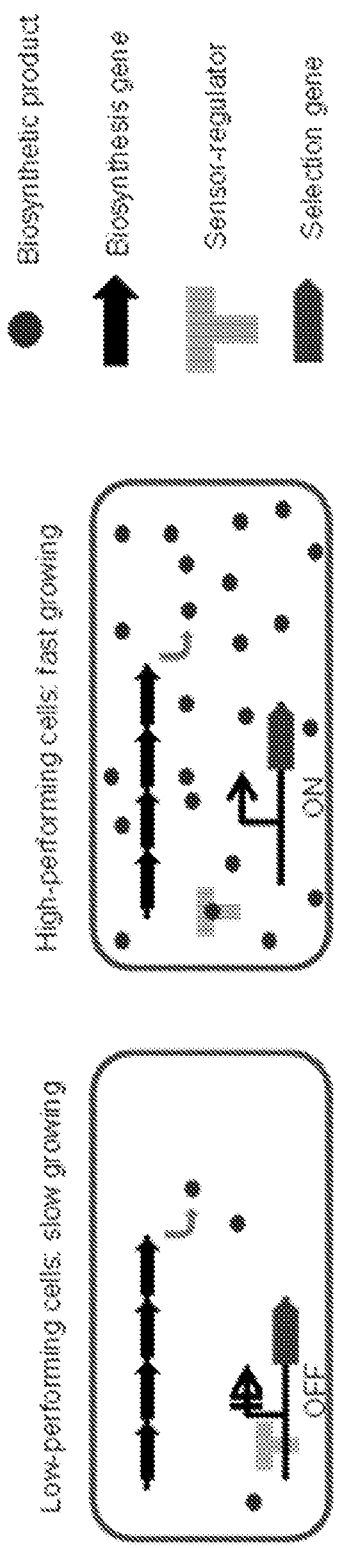
FIG. 11 depicts a design principle of in vivo population quality control (PopQC) in accordance with the present disclosure.
Figure 13A:
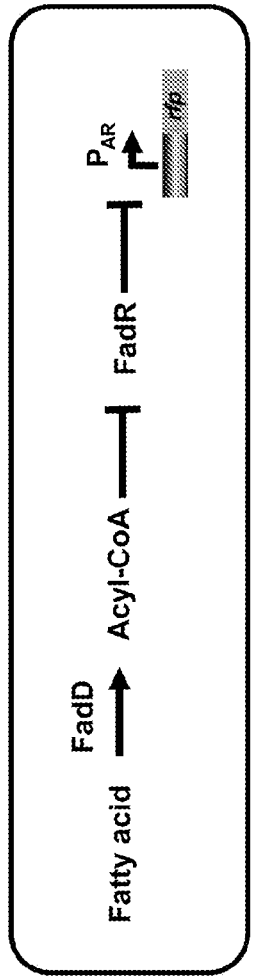
FIGS. 13A and 13B depict characterization of a FFA biosensor in accordance with the present disclosure.
Figure 13B:
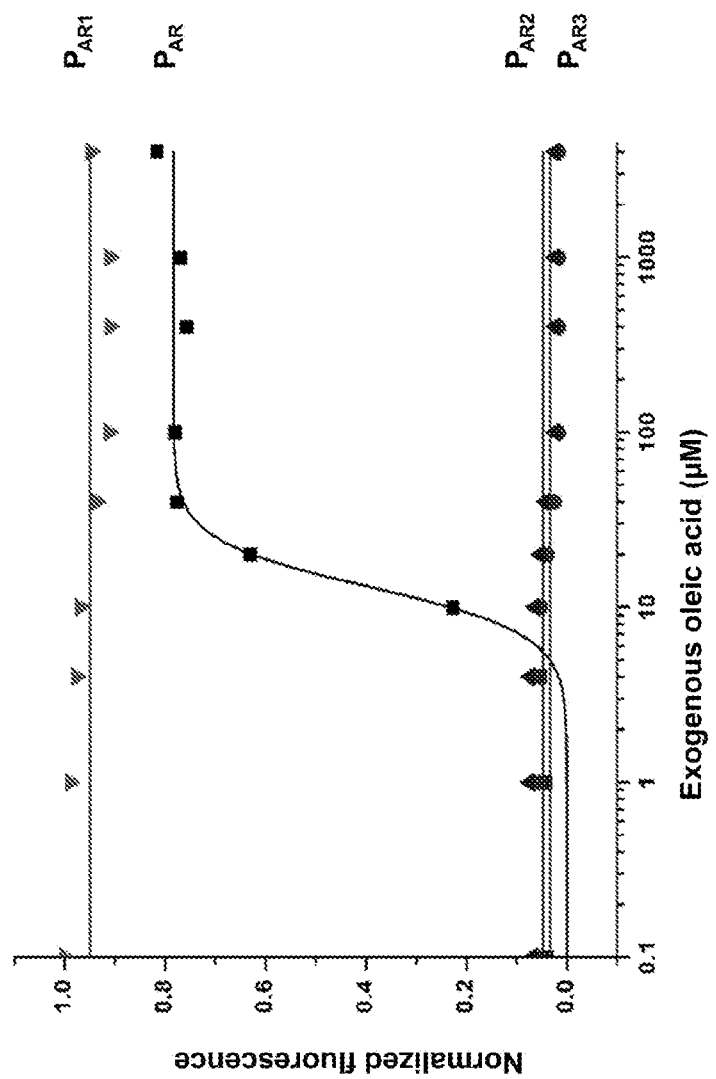
Figure 14:
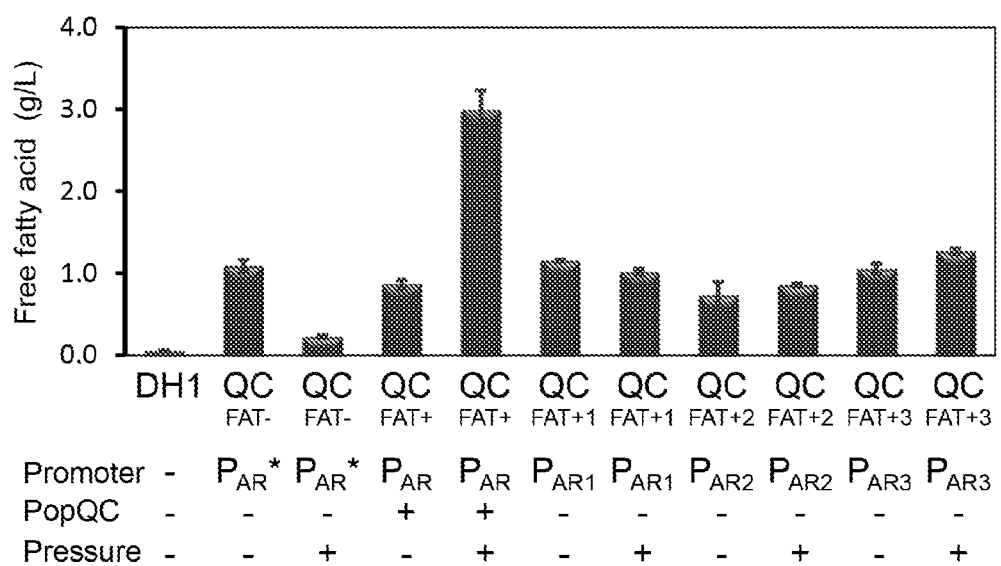
FIG. 14 depicts overall FFA production by engineered cells in accordance with the present disclosure.
Figure 15:
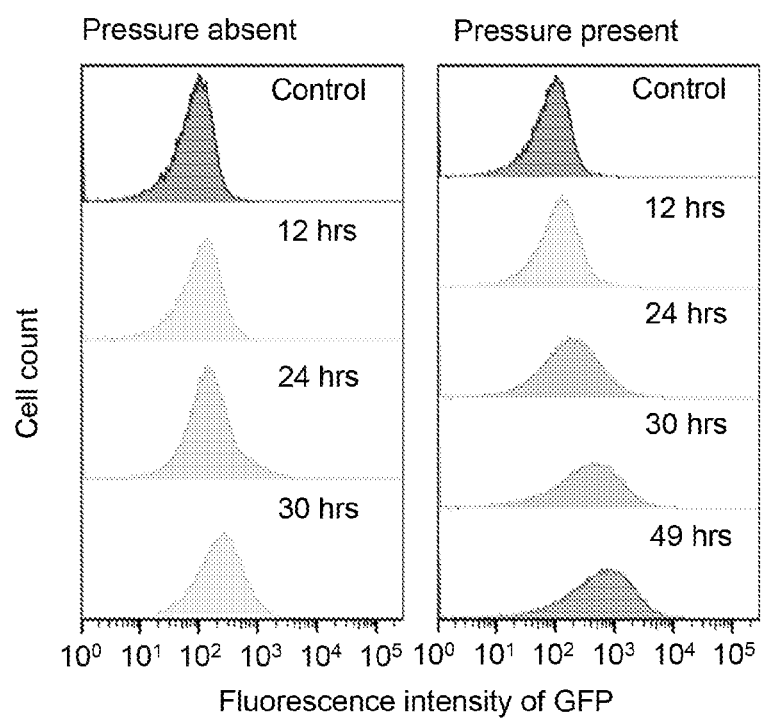
FIG. 15 depicts selection gene expression for a PopQC strain in accordance with the present disclosure.
Figure 16C:
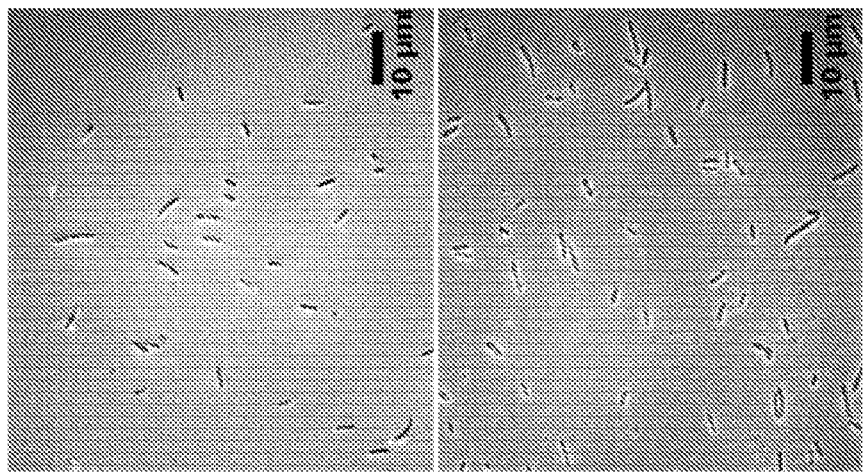
FIGS. 16A-16C depict microscopy images of a PopQC strain in accordance with the present disclosure.
Figure 16B:
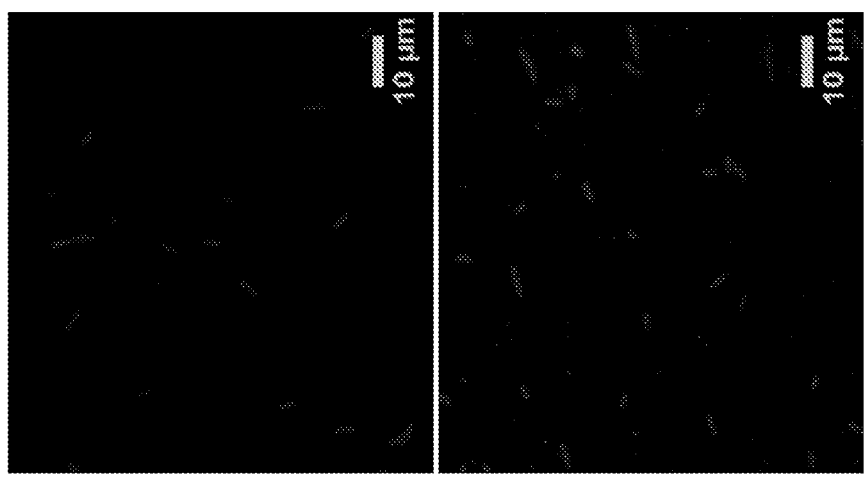
Figure 16A:
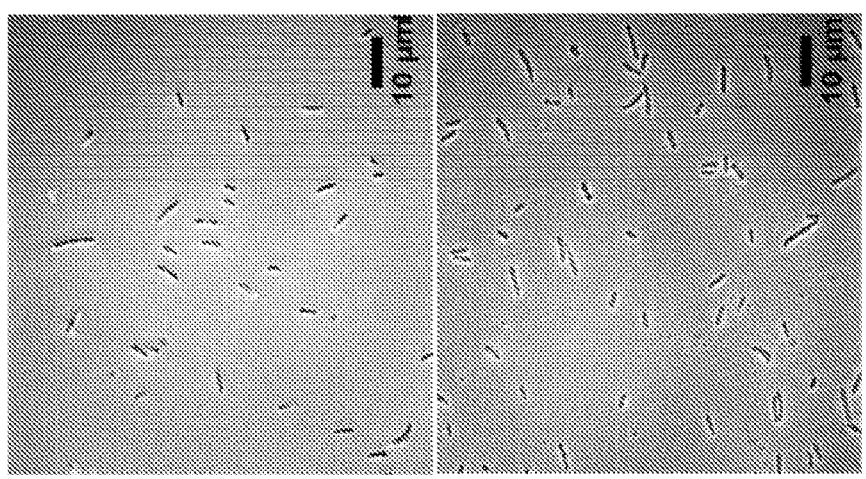
Figure 17A:
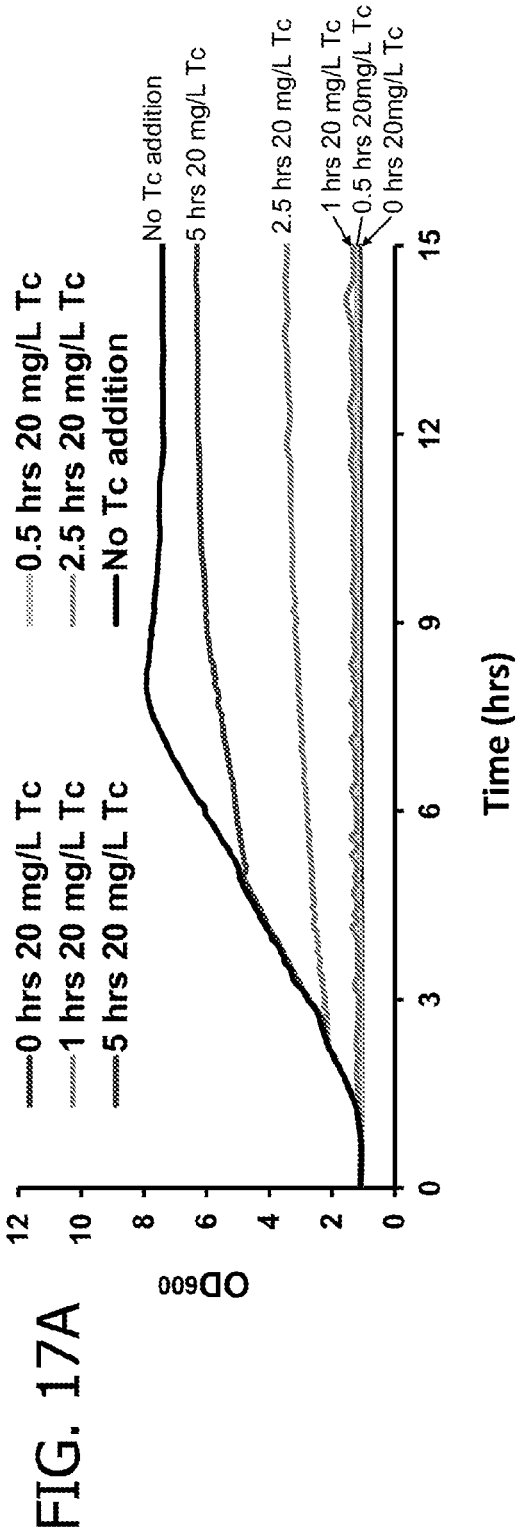
FIGS. 17A and 17B depict strain response to a single tetracycline (Tc) concentration added at different time points in accordance with the present disclosure.
Figure 17B:
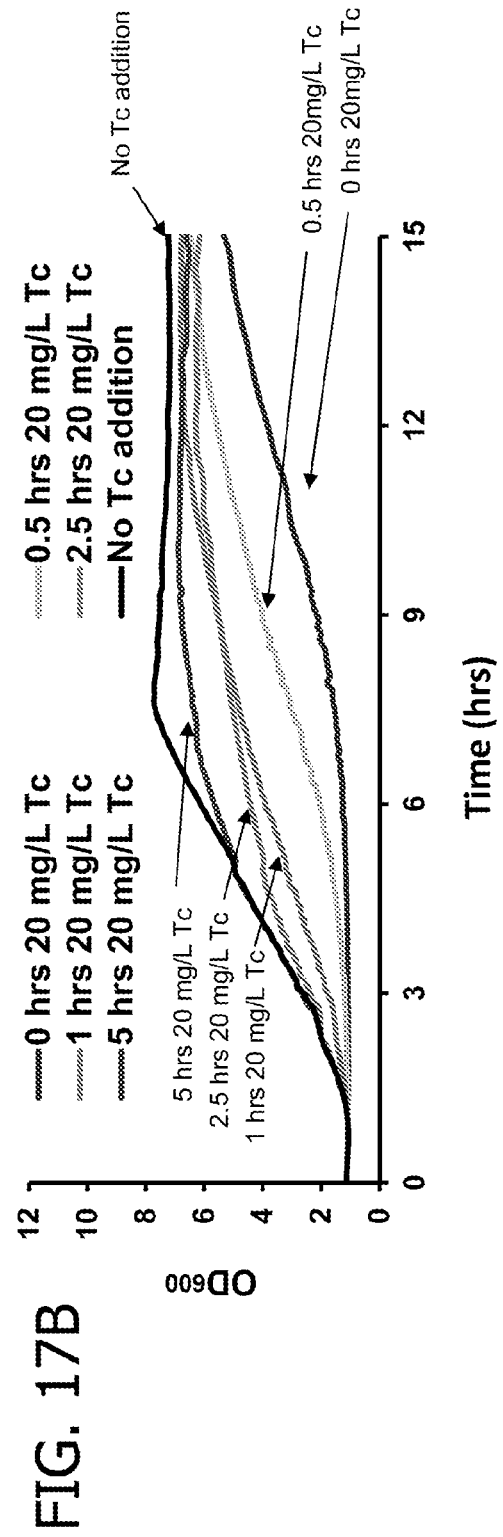
Figure 18A:
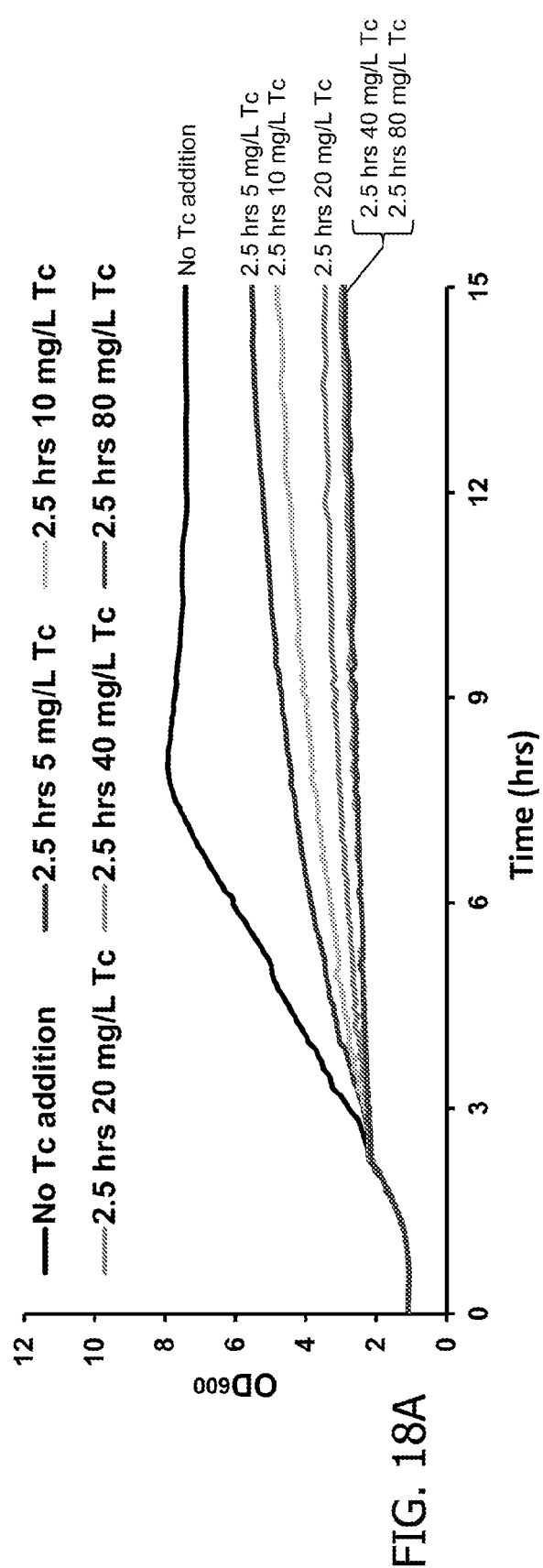
FIGS. 18A and 18B depict strain response to various tetracycline (Tc) concentrations added at a single time point in accordance with the present disclosure.
Figure 18B:
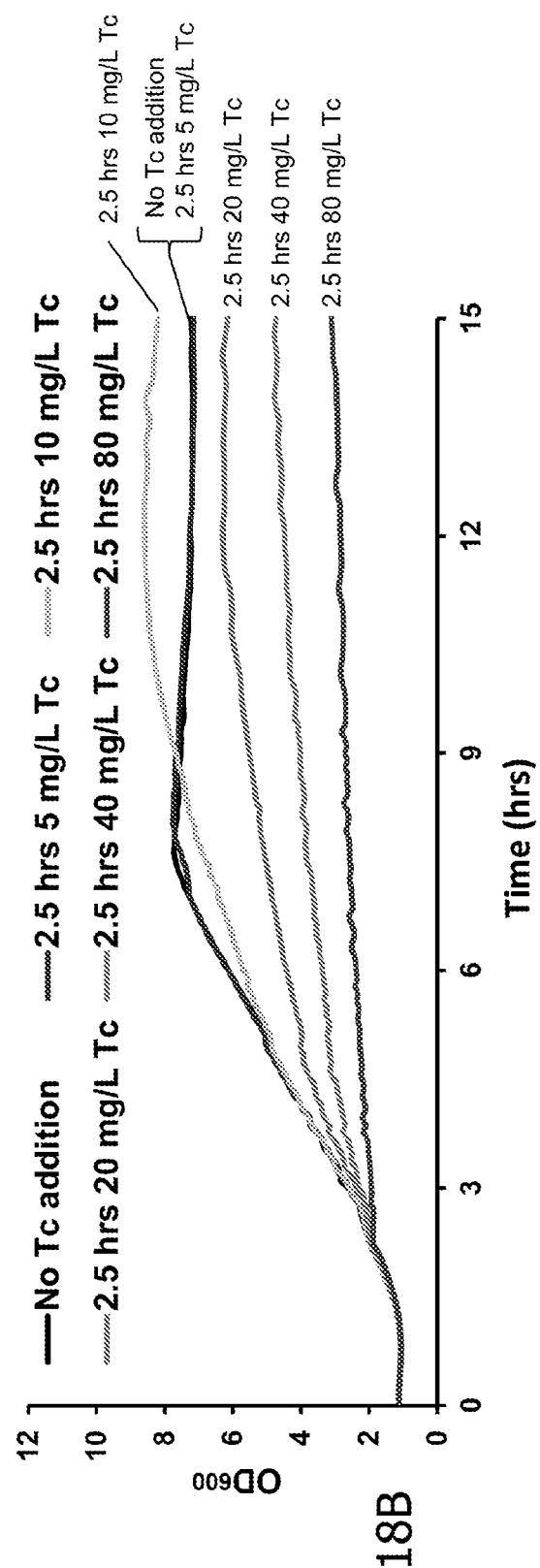
Figure 20A:
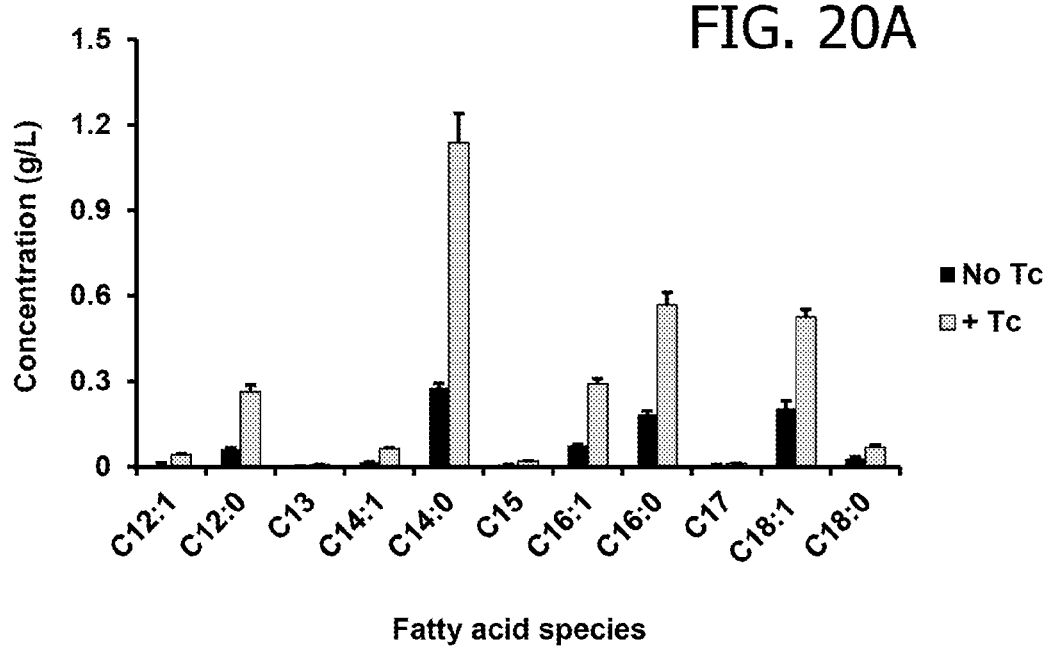
FIGS. 20A and 20B depict FFA chain length profiles produced by a PopQC strain in accordance with the present disclosure.
Figure 20B:
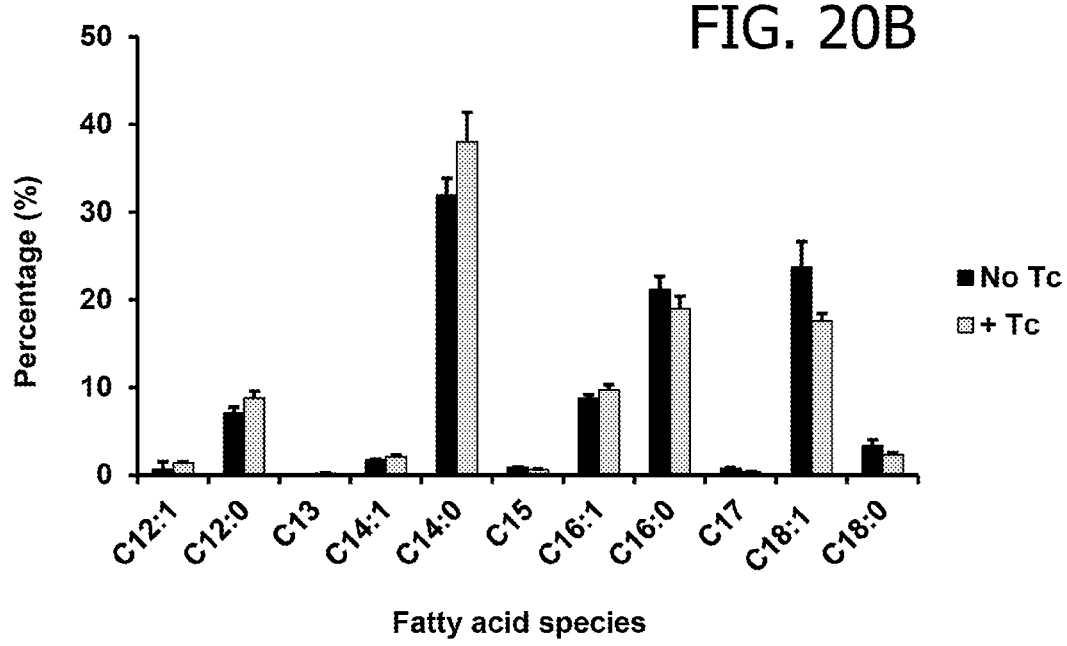

Product titer positively correlates with cell fitness and allows high-performing variants to dominate a system population. The system, termed in vivo population quality control (PopQC), contains a sensor-regulator that continuously monitors product titer and correspondingly regulates selection genes in each cell, thus providing a growth advantage to high-performing cells via a mechanism to overcome a given selection pressure (FIG. 11). FIGS. 11 and 12 depict the design principle of PopQC. FIG. 11 shows that a growth advantage is conferred to high-performing cells. PopQC employs a sensor-regulator that continuously detects the target product and accordingly activates expression of selection genes under corresponding pressures, thereby selectively increasing the fitness of high-performing variants and increasing their proportion in the whole population. FIG. 12 shows PopQC applied to the FFA biosynthetic pathway. A FFA-responsive sensor-regulator, which responds to FFA via acyl-CoA, FadR, and a synthetic promoter $P_{AR}$ (FIG. 12), was used to regulate the expression of a tetracycline efflux protein (encoded by tetA). In the presence of tetracycline, high-performance cells can out-compete low-performance cells and finally dominate the population. Native enzymes and pathways (central pathway, Acc, FabA/B/D/F/G/H/I/Z, and FadD), engineered enzymes (TesA), and regulations (FadR) are shown. PopQC was first applied to FFA overproduction by employing a previously engineered FFA sensor-regulator. The sensor-regulator consists of a transcription factor (TF) FadR, whose DNA-binding activity is regulated by acyl-CoAs (derived from FFA by an acyl-CoA synthetase), and a synthetic promoter $P_{AR}$ that is repressed by FadR (FIGS. 12, 13A, and 13B). The FFA sensor-regulator provided tight control of gene expression from $P_{AR}$ and exhibited 60-fold maximal activation upon the detection of FFA. $P_{AR}$ was cloned to control the expression of a tetracycline (Tc) resistance gene, tetA. The PopQC FFA sensor-regulator was first introduced into a β-oxidation deficient (ΔfadE) E. coli DH1, giving strain $QC_{FAT}$ (see FIG. 1). Along with FIG. 5, FIGS. 14, 15, and 16A-16C depict PopQC improvement of FFA overproduction. FIG. 5 showed that PopQC conferred product-dependent cell growth to engineered cells. The strain $QC_{FAT}$ was cultivated in a minimal glucose medium supplemented with varied amounts of exogenous FFA (oleic acid, 2-1000 µM) in the presence/absence of selection pressure. FIG. 14 illustrates overall FFA produced by engineered cells in cultures both with (+) or without (−) PopQC and selection pressure. Promoters used to control the expression of tetA in each strain are listed. $P_{AR}$ is a FFA-activated promoter, while the promoters $P_{AR1}$, $P_{AR2}$, and $P_{AR3}$ do not respond to FFA. FIG. 15 graphically illustrates expression of the selection gene in PopQC strain. A fast-folding GFP gene was cloned in the same cistron following the selection gene tetA, resulting in strain $QC_{FAT+G}$ (harboring both the FFA biosynthetic pathway and PopQC). The strain was cultivated with or without selection pressure and samples were collected at different points. A control strain DH1 without GFP was used. Single cell fluorescence was analyzed directly by a flow cytometer. FIGS. 16A-16C show microscopy images of strain $QC_{FAT+G}$ with or without selection pressure. Cells were grown to the stationary phase and stained by Nile Red (250 µg/L). Phase contrast (FIG. 16A), fluorescence (FIG. 16B), and phase contrast/fluorescence overlay (FIG. 16C) images of the cells in the absence (top) or presence (bottom) of selection pressure are shown. The ensemble growth rates of $QC_{FAT}$ increased with extracellular FFA concentration in the presence of Tc pressure (FIG. 5), indicating that PopQC effectively provides a growth advantage to FFA-high-producing variants. Next, the FFA biosynthetic pathway was introduced into strain $QC_{FAT}$, giving strain $QC_{FAT+}$. A series of Tc concentrations and delay times (between induction of FFA production and Tc addition) were tested (FIGS. 17A, 17B, 18A, and 18B). FIGS. 17A and 17B, as well as FIGS. 18A and 18B depict responses of strains $QC_{FAT-}$ and $QC_{FAT+}$ to various concentrations of Tc added at different time points. The FFA-producing strain $QC_{FAT+}$ (harboring PopQC to control the Tc-resistance gene tetA) and its control strain $QC_{FAT-}$ ($QC_{FAT+}$ without tetA) were cultivated and monitored in 96-well plates. The cells were induced for FFA production and Tc was added at different concentrations and time points as indicated. A fixed final concentration of Tc (20 mg/L) was added to strains QC$_{FAT-}$ (FIG. 17A) or QC$_{FAT+}$ (FIG. 17B) at 0, 0.5, 1, 2.5, and 5 hours post-induction (PI). Alternatively, varied final concentrations of Tc (0, 5, 10, 20, 40 or 80 mg/L) were added at a fixed time point (2.5 hours) to strains QC$_{FAT-}$ (FIG. 18A) and QC$_{FAT+}$ (FIG. 18B). Tc addition at high concentrations or at early time points seriously retarded cell growth, while Tc addition at low concentrations or at late time points had relatively minor growth effects. A final concentration of 20 mg/L Tc at 2.5 hours PI was adopted for subsequent experiments. Under the selected conditions (20 mg/L Tc, delay time 2.5 hours), strain QC$_{FAT+}$ produced 3.0 g/L of FFA, representing a 3-fold enhancement over QC$_{FAT+}$ without the selection pressure (0.9 g/L) and over the control strain QC$_{FAT-}$ without PopQC (1.1 g/L, FIG. 14). FFA conversion yields during production are given in FIGS. 19A and 19B. FIGS. 19A and 19B depict the time-dependent conversion yield of strain QC$_{FAT+}$. The FFA-producing strain QC$_{FAT+}$ harboring PopQC was grown in the minimal glucose (Glu) medium, induced with IPTG (t=0 hours), and treated with (FIG. 19B) or without Tc (FIG. 19A). Tc addition is indicated by an arrow at 2.5 hrs in FIG. 19B. Glu (squares) and fatty acid (circles) in each sample were measured by HPLC and GC-MS, respectively. Conversion yields (ΔFFA/ΔGlu, ≥0) at each point are shown at right. ΔFFA is the FFA titer at the current time point subtracted by the titer at the previous time point; ΔGlu is the Glu titer at a previous time point subtracted by the titer at the current time point. In the absence of selection pressure, the conversion yield remained ~0.1 g FFA/g glucose (Glu) consumed in the log-phase. In contrast, PopQC selection maintained a high conversion yield, almost 3-fold higher than that without the selection. This high yield was sustained throughout the production period, finally resulting in a 3-fold increase in overall FFA titer (FIGS. 19A and 19B), without changing the FFA chain length profiles (indicating that the FFA composition was not affected by PopQC under the current conditions, FIGS. 20A and 20B). FIGS. 20A and 20B depict FFA profiles produced by strain QC$_{FAT+}$. Concentrations (FIG. 20A) and percentages (FIG. 20B) of free FFA produced by QC$_{FAT+}$ in the absence (black columns) or presence (grey columns) of Tc. The results show that the FFA compositions from Tc-treated and non-Tc-treated cultures were not substantially changed, which indicates responses of FFA-PopQC are related only to the FFA titer (not the FFA composition) in the current conditions. Furthermore, to prove that PopQC functioned via the product-activated sensor-regulator, P$_{AR}$ in the strain QC$_{FAT+}$ was replaced by one of the P$_{AR}$ variants, P$_{AR1}$, P$_{AR2}$, or P$_{AR3}$, which cannot be activated by FFA (FIGS. 13A and 13B), giving strains QC$_{FAT+1}$, QC$_{FAT+2}$, and QC$_{FAT+3}$, respectively. FIGS. 13A and 13B depict the construction and characterization of the FFA biosynthetic pathway and FFA biosensor. FIG. 13A is a schematic representation of the FFA biosynthetic pathway with the FFA biosensor. The biosensor consists of a FFA-responsive transcription factor FadR, whose DNA-binding activity is regulated by acyl-CoAs (derived from FFA by an acyl-CoA synthetase, FadD) and a synthetic FFA-activated promoter P$_{AR}$ that is repressed by FadR. FIG. 13B depicts the responses of FFA biosensors to exogenous oleic acid (0.1-4000 μM). Strains BS$_{AR}$, BS$_{AR1}$, BS$_{AR2}$, and BS$_{AR3}$ (FIG. 1), harboring promoters P$_{AR}$, P$_{AR1}$, P$_{AR2}$, and P$_{AR3}$, respectively, were cultivated in a rich medium with varied amounts of oleic acid. Whole culture fluorescence was recorded at 22 hours after oleic acid induction. Regardless of the selection pressure, FFA titers from these control strains were not improved (FIG. 14).

Example 3

Mechanism of PopQC at the single cell level. To estimate the expression of the selection gene tetA, a gfp gene encoding a fast-folding green fluorescent protein was cloned in the same cistron, 3' of tetA in QC$_{FAT+}$, resulting in strain QC$_{FAT+G}$. Measurement of GFP fluorescence by flow cytometry indicated an increased proportion of cells expressing a high level of tetA in the presence of Tc (FIG. 15). Furthermore, the cells treated with or without Tc were stained by Nile Red and imaged by fluorescence microscopy to estimate FFA titer. When treated with Tc, the proportion of cells exhibiting strong fluorescence (a mean pixel density >50) was increased by 14-fold compared to that without Tc treatment (FIGS. 16A-16C), indicating an increase in the subpopulation of high-performers. Finally, a cell distribution model was formulated to describe cell-to-cell variation during FFA production. Consistent with the experimental results, the simulation showed that PopQC selection was able to increase the population of high-performers and thereby improve the ensemble FFA production (FIGS. 6A-6C). FIGS. 6A-6C depict modeled FFA abundance distributions in strains with or without PopQC selection. The model was formulated to describe the production and cell-to-cell variation of FFA under exponential growth phase. Time course of FFA abundance distributions in strains with (FIG. 6B) and without (FIG. 6A) PopQC selection are shown. Time points in the unit of hour are presented above the peaks. FIG. 6C depicts modeled cell growth (left) and overall FFA titer (right) under PopQC selection. Squares represent simulated results and crosses represent experimental measurements. Altogether, these results indicate a mechanism whereby PopQC enhances performance by activating expression of tetA to increase the fitness of high performers, thus enhancing their proportion within a culture under selection pressure.

Example 4

Confirmation of PopQC enhancement of performance by selecting for non-genetic metabolic variants rather than beneficial genetic mutants. To confirm that PopQC enhances performance by selecting for non-genetic metabolic variants rather than beneficial genetic mutants, single offspring colonies of QC$_{FAT+}$ were isolated from both Tc- and non-Tc-treated FFA-producing cultures at different time points. When re-cultivated in the absence of Tc, none of the offspring colonies were able to produce more than 1.2 g/L of FFA, far short of the 3 g/L FFA titer of the PopQC strain (FIGS. 21A and 21B), indicating that the high-performer trait was not genetic. FIGS. 21A and 21B depict the FFA production and genome sequence of offspring colonies. The strain QC$_{FAT+}$ (parent strain) was first cultivated with (FIG. 17B) or without (FIG. 17A) Tc for FFA production. Offspring colonies from these cultures were isolated at different time points (presented above dashed boxes) and subsequently re-cultivated for FFA production in the absence of Tc. Offspring colonies from 72-hour cultures together with the parent strain were subjected to genome sequencing. Genes identified as carrying non-synonymous SNPs (relative to the parent strain) from each group of offspring strains are presented at right, including rplT (50S ribosomal protein L20), purB (adenylosuccinate lyase), yheS (putative ABC transporter ATP-binding protein), rpoC (DNA-directed RNA polymerase subunit beta), hisA (phosphoribosyl-formimino-5-aminoimidazole carboxamide ribotide isomerase), and greA (transcription elongation factor). Summarized details of the genome sequencing results are listed in FIGS. 22A-22U. Furthermore, a group of ten colonies from each culture (Tc treated or non-treated) was selected for genome sequencing, and the results showed only three non-synonymous SNPs in each group, relative to the parent strain $QC_{FAT+}$. These SNPs were confirmed to be unrelated to the improved FFA yield (FIGS. 21A and 21B), and some of them were likely to be mutations in response to the stress conditions used for selection (see tables in FIGS. 22A-22U). Although PopQC can improve titers by selecting for beneficial genetic mutants, the results indicate that in the case of FFA production, PopQC improved titers through selection of non-genetic, metabolic variants. With respect to the genome sequence details shown in FIGS. 22A-22U, the parent strain $QC_{FAT+}$ (FIG. 1) containing three plasmids (FIG. 3) was used for FFA production, and the cell culture was treated with or without Tc. After 72 hrs incubation, offspring colonies QCn (n=16-25) strains were isolated from the non-Tc culture, whereas offspring colonies QCTcn (n=26-35) were isolated from the Tc culture. The offspring colonies and the parent strain (from a freezer glycerol stock) were subjected to genome sequencing. Reads were aligned to the DH1 strain reference genome (Escherichia coli DH1 asm27010v1 GCA_000270105.1.23) with the three plasmids, using Novoalign. All strains had a fadE gene deletion and no DNA mutation is was found in plasmids. In offspring colonies, the non-synonymous SNPs, which are different from those in the parent strain $QC_{FAT+}$, are also given in tables A-U of FIGS. 22A-22U. Standard nucleotide coding includes: R, (A,G); Y(C,T); M, (A,C); K, (G,T); S, (C,G); W, (A,T). Compared to the parent strain $QC_{FAT+}$, four out of ten offspring colonies from the non-Tc-treated culture were found to contain one or two non-synonymous SNPs. All ten offspring colonies from the Tc-treated culture contained one non-synonymous SNP, of which a single nucleotide mutation at rpoC (A->C, leading to an E375A mutation on the corresponding protein, an RNA polymerase subunit) was frequently present. RpoC mutations were reported to be involved in resistance to surfactants and the increase of cell growth rate in a minimal medium. Because bacteria perform genetic mutation for growth fitness under stressful conditions, the rpoC mutation is likely an enriched random mutation caused by Tc treatment and/or FFA overproduction. Consistently, these rpoC mutant strains were able to grow normally in the presence of 20 mg/L Tc, implying the selected colonies had escaped our PopQC system. However, this escaping route did not affect PopQC as improved production was observed. Furthermore, the escaping event can be potentially avoided if other selection methods are employed. No mutation was identified on PopQC components (fadD, fadR, $P_{AR}$-tetA) in any of the offspring strain.

Example 5

Figure 23A:
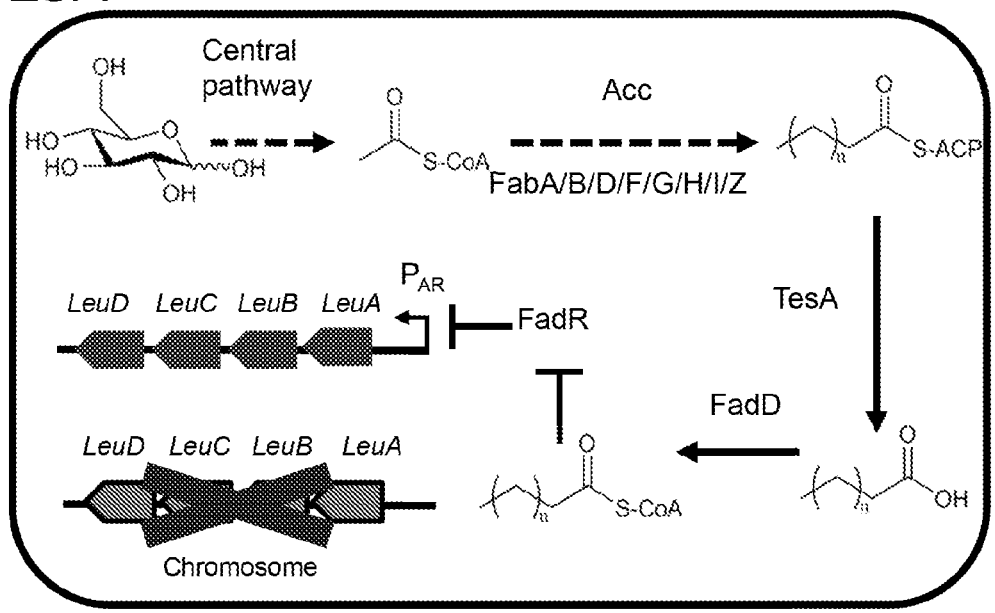
FIGS. 23A and 23B depict an alternative biosynthetic pathway for FFA production in accordance with the present disclosure.
Figure 23B:
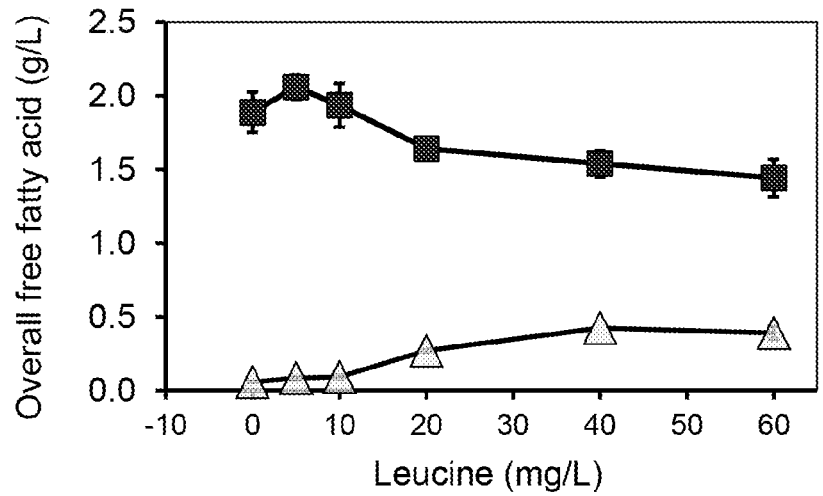
Figure 24A:
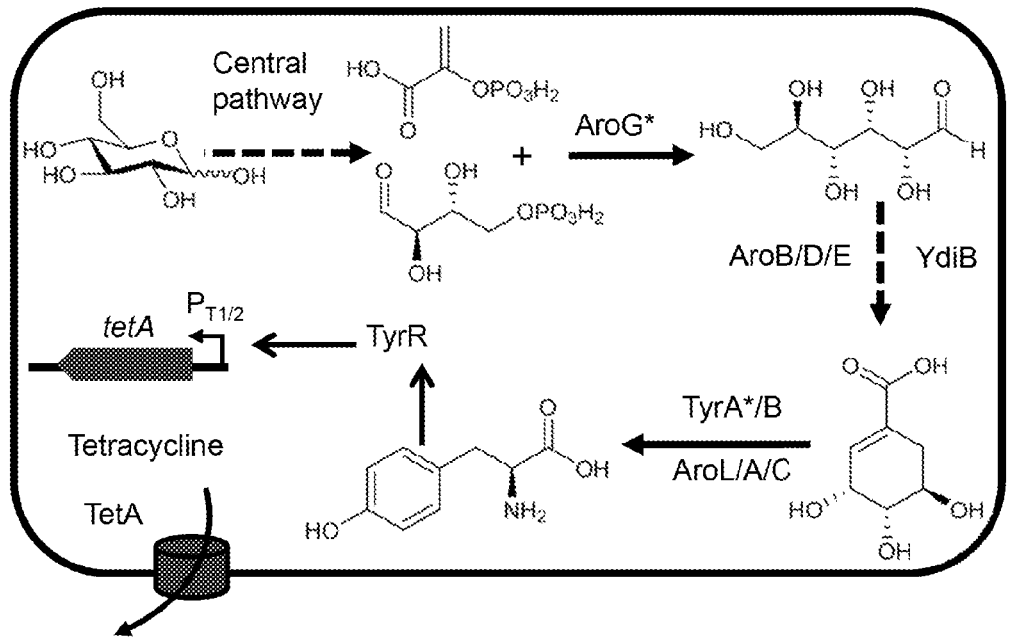
FIGS. 24A and 24B depict a biosynthetic pathway for tyrosine production in accordance with the present disclosure.
Figure 24B:
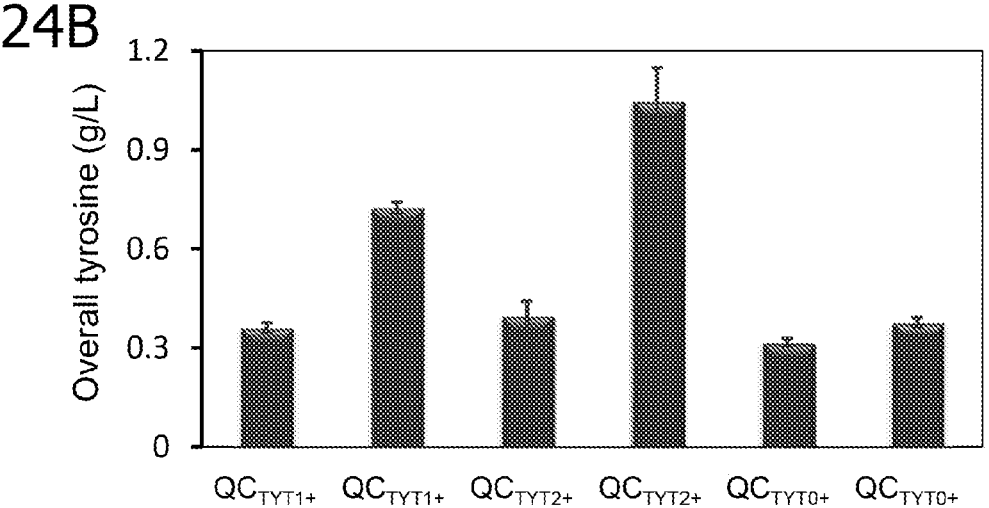
Figure 25A:
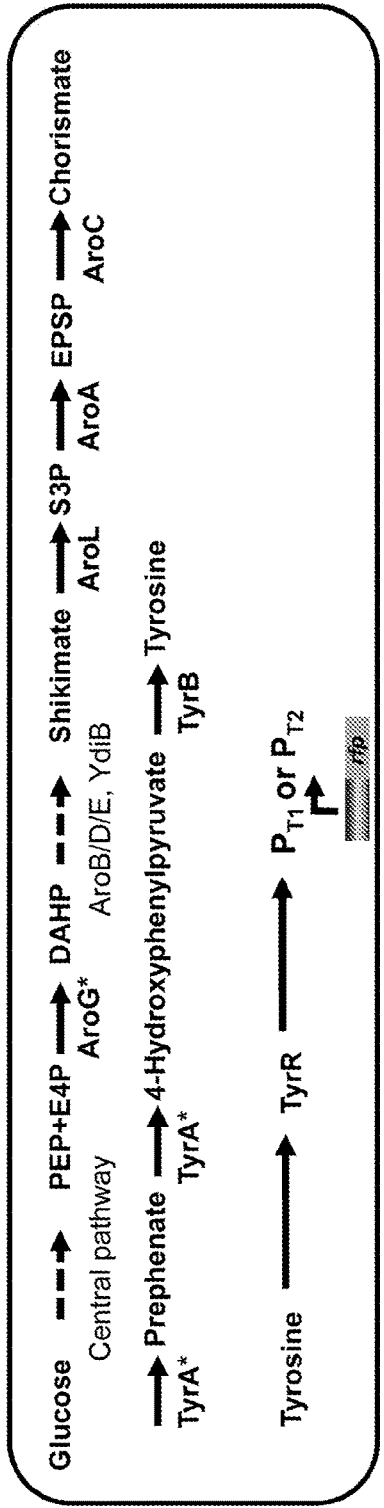
FIGS. 25A and 25B depict construction and characterization for biosensors and a tyrosine biosynthetic pathway in accordance with the present disclosure.
Figure 25B:
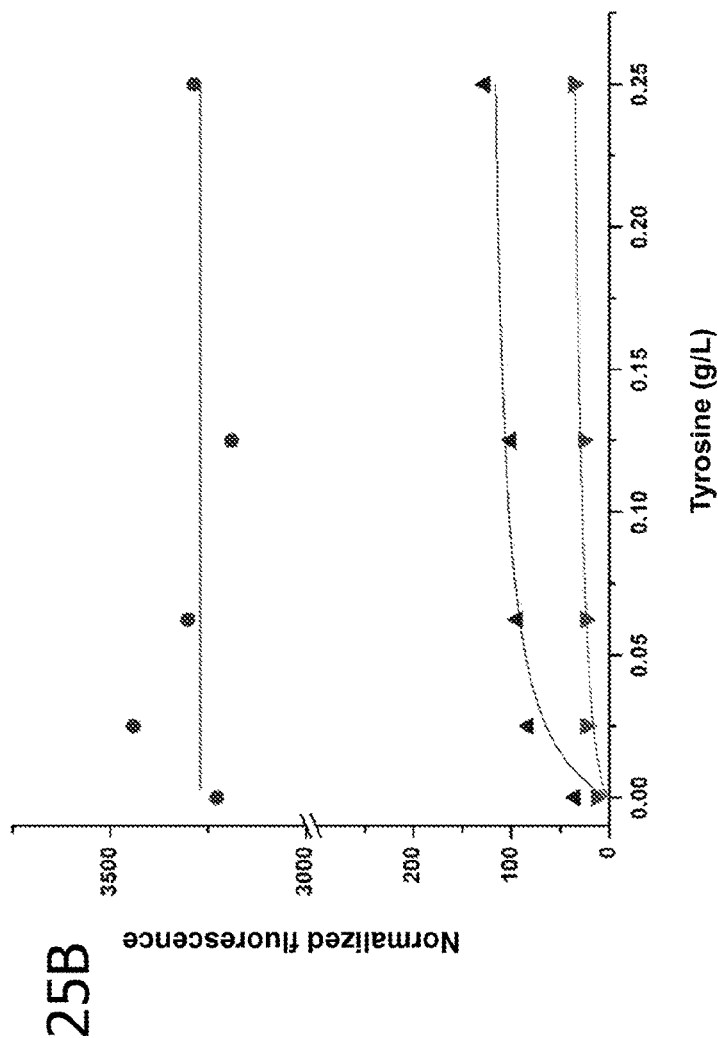
Figure 26:
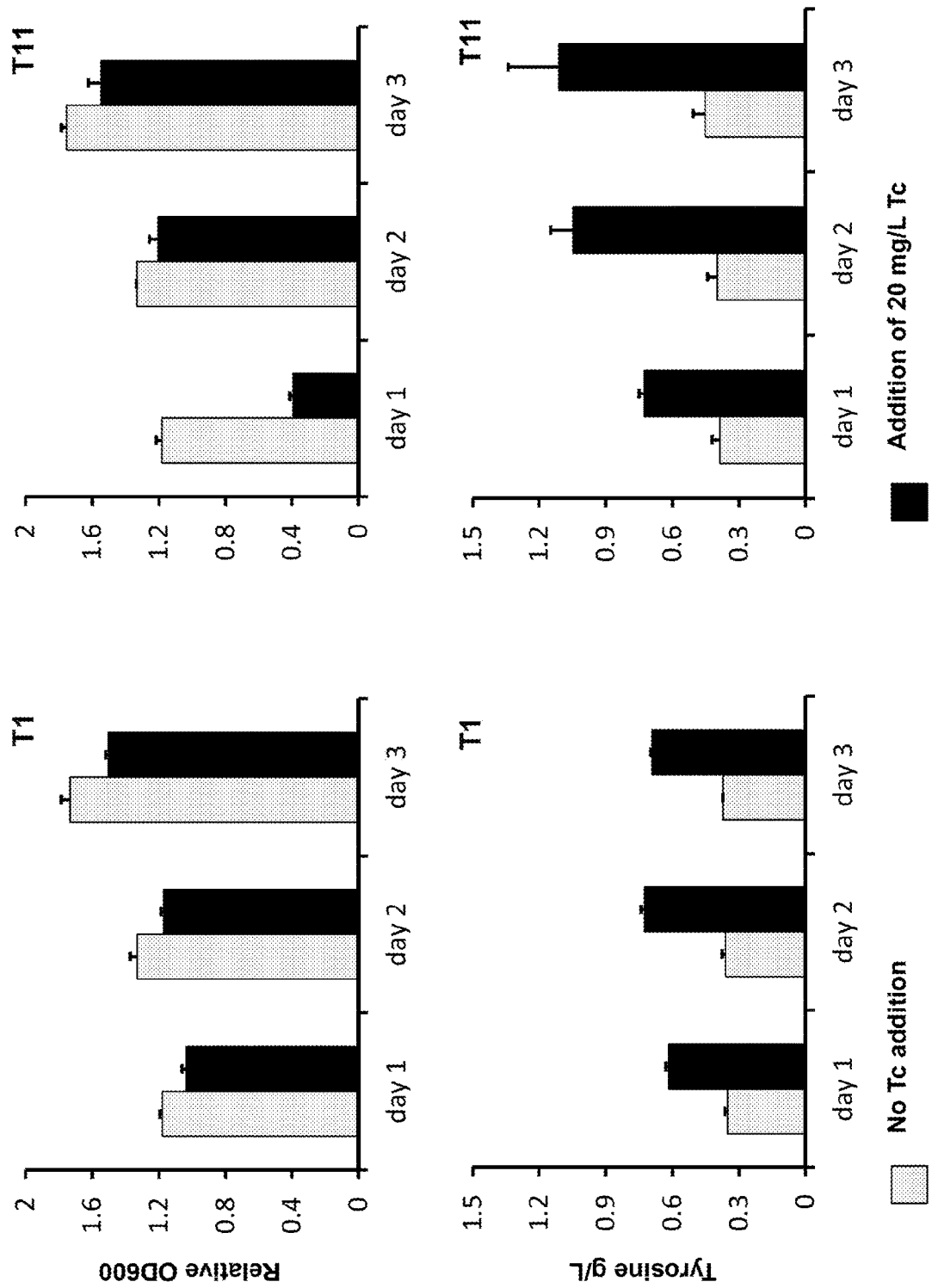
FIG. 26 depicts tyrosine production by PopQC strains in accordance with the present disclosure.

The FFA-activated promoter $P_{AR}$ controls the expression of genes from an essential metabolic pathway (e.g., as an alternative to using expensive and environmentally-problematic antibiotics with an antibiotic resistance gene as the selection gene). FIGS. 23A, 23B, 24A, and 24B depict expansion of the applicability of PopQC. FIG. 23A shows an alternative PopQC pathway for FFA biosynthesis employing an essential leucine biosynthetic pathway encoded by gene operon LeuABCD. The operon was placed under the control of the FFA-activated promoter $P_{AR}$ in a leucine auxotrophic E. coli host (DH10B), resulting in the strain $QC_{FAL+}$. FIG. 23B shows FFA produced from the strain $QC_{FAL+}$ (squares) and a control strain $QC_{FAL-}$ (without PopQC, triangles). Both strains were cultivated in parallel for FFA production in the minimal glucose medium containing various concentrations of leucine (0-60 mg/L). FIG. 24A illustrates improvement of tyrosine production by PopQC. A tyrosine-responsive TF TyrR and a tyrosine-activated promoter $P_{T1}$ or $P_{T2}$ (FIGS. 25A and 25B) were used to regulate the expression of tetA. PEP, phosphoenolpyruvate; E4P, erythrose-4-phosphate; DAHP, 3-deoxy-D-arabinoheptulosonate-7-phosphate. In both FIG. 23A and FIG. 24A, native pathways and enzymes (central pathways, Acc, FabA/B/D/F/G/H/I/Z, FadD, LeuDLeuCLeuBLeuA Chromosome, AroB/D/E, and YdiB), engineered pathways (TesA, AroG*, TyrA*/B, and AroL/A/C), selection genes (LeuDLeuCLeuBLeuA selection genes, and tetA selection gene with resulting TetA efflux pump), and regulations (FadD and TyrR) are shown. FIG. 24B illustrates tyrosine produced by engineered cells in cultures both with (+) or without (-) PopQC and selection pressure. Both promoters $P_{T1}$ and $P_{T2}$ are tyrosine-activated promoters, whereas promoter $P_{T0}$ does not respond to tyrosine. Specifically, tetA was replaced with a leucine biosynthetic operon and inserted the resulting PopQC construct along with the FFA pathway into a leucine auxotrophic E. coli strain, DH10B (FIG. 23A). The resulting strain $QC_{FAL+}$ produced 2.0 g/L of FFA in a leucine-deplete minimal medium, which was 40% higher than $QC_{FAL+}$ cultured in a leucine-replete medium (1.4 g/L FFA), and 5-fold higher than the control strain $QC_{FAL-}$ without PopQC in the leucine-replete medium (FIG. 23B). These results demonstrated that PopQC can be used to enhance product yield in a cost-effective and industrially-relevant manner. FIG. 26 depicts tyrosine production by strains $QC_{TYT1+}$ and $QC_{TYT2+}$. PopQC strains $QC_{TYT1+}$ and $QC_{TYT2+}$ harboring promoters $P_{T1}$ and $P_{T2}$, respectively, were grown in minimal glucose medium for tyrosine production. The relative OD and tyrosine titers were measured over three days. Black bars, with selection pressure (20 mg/L of Tc); grey bars, no selection pressure.

Example 6

Construction of a PopQC system for overproduction of tyrosine, a high-value amino acid, showed the ubiquity of biosynthetic variation and the broad applicability of PopQC. FIGS. 25A and 25B depict the construction and characterization of the tyrosine biosynthetic pathway and biosensors. FIG. 25A depicts the biosynthetic pathway for tyrosine. Single steps (solid arrows), multiple steps (dashed arrows). Enzymes: AroG* (D146N), feedback-resistant DAHP synthase; AroL, shikimate kinase II; AroA, EPSP synthase; AroC, chorismate synthase; TyrA* (M531; A354V), feedback-resistant chorismate mutase/prephenate dehydrogenase; TyrB, tyrosine aminotransferase; TyrR, tyrosine-responsive transcriptional factor; AroB, dehydroquinate synthase; AroD, dehydroquinate dehydratase; AroE, shikimate dehydrogenase; YdiB, quinate/shikimate dehydrogenase. Metabolites: PEP, phosphoenolpyruvate; E4P, erythrose-4-phosphate; DAHP, 3-deoxy-D-arabinoheptulosonate-7-phosphate; S3P, shikimate-3-phosphate; EPSP, 5-enolpyruvylshikimate-3-phosphate. Native pathways and enzymes (central pathway, AroB/D/E, and YdiB); engineered pathways (AroG*, AroL, AroA, AroC, TyrA*, and TyrB), and regulations (TyrR) are shown. FIG. 25B depicts the responses of synthetic biosensors to exogenous tyrosine. An rfp reporter gene was cloned 3' of promoters $P_{T0}$ (circles), $P_{T1}$ (up-pointing triangles), and $P_{T2}$ (down-pointing triangles), respectively. Strains harboring each biosensor were cultivated in the minimal glucose medium containing varied amounts of tyrosine (0-0.25 g/L) and the culture fluorescence was recorded at 36 hours. The results show that such tyrosine biosensors can respond to concentrations up to 0.25 g/L tyrosine, close to tyrosine's water solubility. Two tyrosine-activated synthetic promoters $P_{T1}$ and $P_{T2}$ (FIG. 25 and FIG. 4), controlled by a tyrosine-responsive TF TyrR, were cloned to regulate the expression of tetA (FIG. 24A). FIG. 4 summarizes tyrosine-responsive DNA boxes. TyrR is a tyrosine-responsive transcription factor involved in tyrosine biosynthesis. In the absence of tyrosine, TyrR forms a dimer and binds to specific DNA sites called strong boxes. In the presence of tyrosine, TyrR forms a hexamer and binds to both the strong boxes and specific lower-affinity DNA sequences called weak boxes. The strong and weak TyrR boxes from native TyrR-mediated promoters $P_{tyrP}$ (a repressor), $P_{aroP}$ (a repressor), and $P_{mtr}$ (an activator), were chosen for construction of synthetic promoters $P_{T0/1/2}$. The promoter $P_{T0}$ contains TyrR boxes aroP1 and tyrP2, while the promoters $P_{T1}/P_{T2}$ contain TyrR boxes mtr1 and mtr2. When these PopQC constructs were introduced into a tyrosine-overproducing strain (giving $QC_{TYT1+}$ and $QC_{TYT2+}$), the presence of Tc enhanced tyrosine yield by 2.0 and 2.6-fold, respectively (FIG. 24B and FIG. 4). In contrast, when the tyrosine-activated promoter was replaced by the promoter $P_{T0}$, which is non-responsive to tyrosine, no enhancement in tyrosine yield was observed. Moreover, we found that strain $QC_{TYT2+}$, with a lower promoter activity, exhibited better performance than strain $QC_{TYT1+}$ (FIG. 24B and FIG. 26), implying that a more stringent selection pressure can further increase the effectiveness of PopQC. Alternatively, tuning the detection ranges of biosensors by changing the $K_d$ (dissociation constant) of TF to product may overcome saturation of biosensors and further improve the effects of PopQC.

Example 7

Figure 27A:
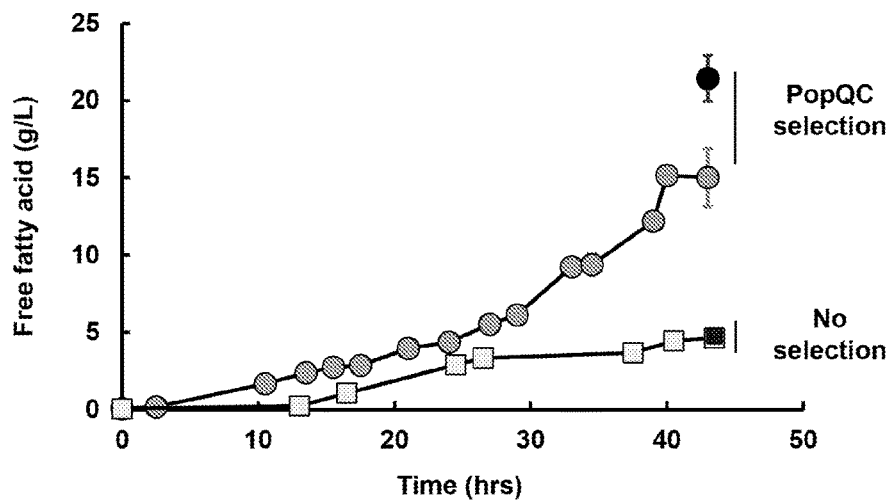
FIGS. 27A and 27B depict FFA production and growth for fed-batch PopQC cultures in accordance with the present disclosure.
Figure 27B:
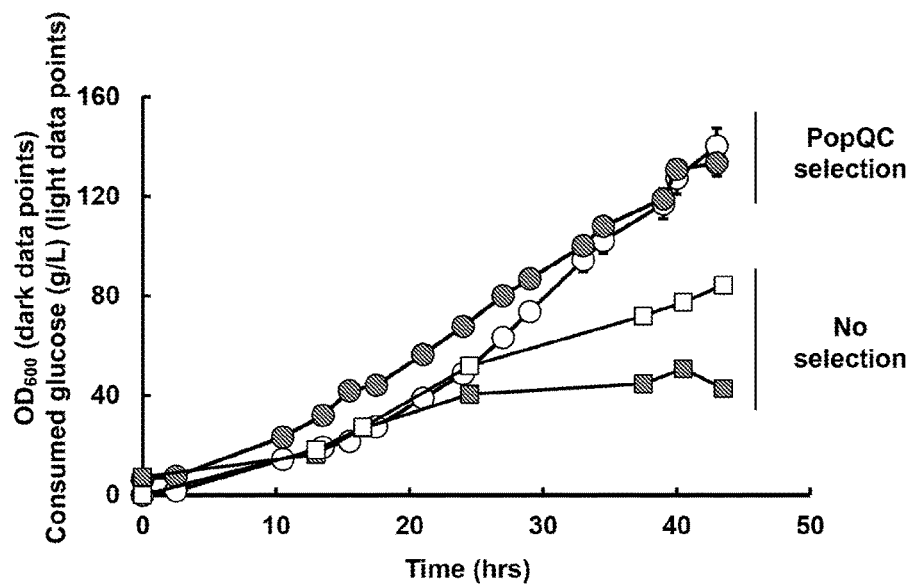

PopQC strain $QC_{FAL+}$ in a long-term fermentation process. Fed-batch fermentation was carried out using a New Brunswick Bioflo 110 fermenter with a pH meter, a dissolved oxygen electrode, and a temperature electrode. An overnight LB culture of the strain $QC_{FAL+}$ (2% inoculum) was inoculated into 0.45 L batch medium (minimal M9 glucose medium) with 10 mg/L leucine and appropriate antibiotics. Fermentation temperature was set to 35° C. and pH was controlled at 7.4 by feeding 6N ammonium hydroxide via an auto-pump. When cell density reached 6.2 (time=0 hrs), 0.5 mM IPTG along with 0.02% (V/V) antifoam 204 (Sigma) were added into the fermentation cell culture. Flow rate of air was kept at around 1.5 L/min and stirring speed was maintained at 400-550 rpm. Feeding medium (400 g/L glucose and 12 g/L MgSO4) was fed to the fermentation culture 1 hrs post induction (with feeding rate of 7.38 µL/min (time=1 hrs), 13.27 µL/min (time=11 hrs), 48.95 µL/min (time=13 hrs), 61.25 µL/min (time=18 hrs), and 97.30 µL/min (time=24.5 hrs). Broth samples (2-3 mL) were collected at a series of time points to measure cell density and store at −20° C. for further measurements of residual glucose and FFA production. During fermentation, floating dead cells or fatty acid particles were found to be stuck to the upper inner wall of the fermenter. FIGS. 27A and 27B depict employing PopQC in a fed-batch FFA-producing culture. FIG. 27A depicts FFA production in fed-batch culture of the strain $QC_{FAL+}$ using a minimal medium. In FIG. 27A, the black circle data point and black square data point represent overall FFA at the end of fermentation. FIG. 27B depicts OD (dark data points) and consumed glucose (light data points) in the fed-batch culture. After fermentation (time=43 hrs), all these were re-suspended in the fermentation culture to accurately measure overall FFA production (shown in FIG. 27A as black data point circle and square). After induction, FFA production and cell density (OD) increased along with consumption of carbon source glucose (FIGS. 27A and 27B). At the end of the fermentation process (43 hrs post induction), the broth of the fermentation culture contained 15.0 g/L FFA, and the overall fermentation sample (including the culture broth and floating fatty acids and cell particles) contained 21.5 g/L FFA. Accordingly, PopQC enhanced the performance of FFA-producing fermentation to an exceptionally high level (21.5 g/L FFA titer, 0.5 g/L/hrs productivity, and 0.15 g FFA/g glucose yield—43% of the maximal yield), which is substantially better than any previously reported FFA fermentation performance. The PopQC system also drives host cells to maintain production capacity to survive under the PopQC selection pressure during a long-term fermentation process. Thus, this essential-gene-enabled selection system can be used to enhance product yield in a cost-effective and industrially-relevant manner. PopQC can improve biosynthetic performance and is generally applicable for biosynthetic production given the ubiquity of the variation and the availability of biosensors for a wide array of valuable bioproducts. Furthermore, because the metabolic burden caused by bioproducts or the expression of heterologous pathways can impose a fitness disadvantage on high-performers, PopQC provides even greater enhancement of performance in bioproduction scenarios where a metabolic burden is present.

In summary, effective tools to enhance biosynthetic performance are essential to realizing cost-effective biosynthesis. Past strategies for enhancement of biosynthetic performance may have overlooked the potential effects of non-genetic variation or assumed that isogenic cell cultures are phenotypically uniform. According to the present disclosure, biosynthetic performance can vary greatly between subpopulations of isogenic cultures. The ubiquity of non-genetic variation suggests that even currently successful traditional approaches to enhance bioproduction may be limited by the presence of low-performance, non-genetic variants. For example, in the case of FFA production in E. coli, most cells exhibit low biosynthetic performance and only a small fraction of the population generates a majority of product. The high prevalence of low performers indicates that non-genetic variation is more than just a source of suboptimal performance should not be ignored when pursuing optimal biosynthesis. Further, for industrial-scale bioproduction it is known that microenvironments (oxygen level, pH and so on) exist on various time scales that can further exaggerate non-genetic variations, making the potential effects of variation significant in industrial bioprocesses. Non-genetic variation can be exploited for many biosynthetic pathways to enrich high performers and enhance ensemble biosynthesis.

The construction of PopQC requires two basic parts: a phenotype-responsive biosensor and a selector. Both parts can and have been obtained from a variety of natural and engineered sources. The simple design and broad applicability of PopQC allows it to be easily combined with traditional approaches to alleviate limitations of non-genetic variation and further enhance biosynthesis toward theoretical maxima. In this way, the design principle of PopQC allows it to be useful for improving other desired phenotypes (for example, protein overproduction, disease treatment, bioremediation and genetic logic), given an appropriate biosensor corresponding to the desired phenotype. Thus, PopQC may serve as a supplement to existing technologies as well as a standalone technology to enhance performance. PopQC host cells, systems, and methods described herein can effectively exploit non-genetic cell-to-cell variation for enhanced biosynthesis.

When introducing elements of the present disclosure or embodiments thereof, the articles "a," "an," "the," and "said" are intended to mean that there are one or more of the elements. The terms "comprising," including," and "having" are intended to be inclusive and mean that there may be additional elements other than the listed elements.

In view of the above, it will be seen that the several advantages of the disclosure are achieved and other advantageous results attained. As various changes could be made in the above processes and composites without departing from the scope of the disclosure, it is intended that all matter contained in the above description and shown in the accompanying drawings shall be interpreted as illustrative and not in a limiting sense.

What is claimed is:

1. An *Escherichia coli* (E. coli) host cell expressing a DNA-directed RNA polymerase, and comprising:
  a) a first nucleic acid molecule encoding at least one product-responsive transcription factor selected from the group consisting of FadR, TyrR, BenM, AIkS, Xy1 R, CdaR, FapR, BadR, MarR, EmrR, CbaR, MetJ, GR, NagC, CynR, BmoR, NodD, MdcR, CatR, theophylline riboswitch, ammeline riboswitch, thiamine pyrophosphate riboswitch, and AdoCbl riboswitch; and
  b) a second nucleic acid molecule comprising:
    i) a promoter recognized by the DNA-directed RNA polymerase, operably linked to an antibiotic resistance gene, wherein the promoter is selected from the group consisting of $P_{AR}$, $P_{BAD}$, $P_{LacUV5}$, $P_{mtr}$, $P_{T1}$, and $P_{T2}$; and
    ii) a product-responsive transcription factor binding site that binds to the product-responsive transcription factor;
      wherein the product-responsive transcription factor binding site is operably linked to the promoter;
      wherein when the product-responsive transcription factor binds to the product-responsive transcription factor binding site in the absence of a product, promotor activity is repressed and expression of the antibiotic resistance gene is blocked; and
      wherein when the product-responsive transcription factor binds to the product-responsive transcription factor binding site in the presence of the product, promotor activity is activated and the antibiotic resistance gene is expressed.

2. The cell of claim 1, wherein the product is an endogenously produced product.

3. The cell of claim 1, wherein the product is a free fatty acid (FFA).

4. The cell of claim 1, wherein the product-responsive transcription factor is FadR.

5. A method for selection of non-genetic metabolic variants of *Escherichia coli* (E. coli) host cells that are high-producers of a product, the method comprising:
  culturing the E. coli host cells to express a DNA-directed RNA polymerase, wherein each E. coli host cell comprises:
    a product-responsive transcription factor selected from the group consisting of FadR, TyrR, BenM, AIkS, Xy1R, CdaR, FapR, BadR, MarR, EmrR, CbaR, MetJ, GR, NagC, CynR, BmoR, NodD, MdcR, CatR, theophylline riboswitch, ammeline riboswitch, thiamine pyrophosphate riboswitch, and AdoCbl riboswitch; and
    a nucleic acid molecule comprising:
      a promoter recognized by the DNA-directed RNA polymerase, operably linked to an antibiotic resistance gene, wherein the promoter is selected from the group consisting of $P_{AR}$, $P_{BAD}$, $P_{LacUV5}$, $P_{mtr}$, $P_{T1}$, and $P_{T2}$; and
      a product-responsive transcription factor binding site operably linked to the promoter, wherein the product-responsive transcription factor binding site binds to the product-responsive transcription factor;
        wherein when the product-responsive transcription factor binds to the product-responsive transcription factor binding site in the absence of a product, promotor activity is repressed and expression of the antibiotic resistance gene is blocked;
        wherein when the product-responsive transcription factor binds to the product-responsive transcription factor binding site in the presence of the product, promotor activity is activated and the antibiotic resistance gene is expressed; and
      wherein the culture comprises the antibiotic, thereby selecting for E. coli host cells that are high-producers of the product.

6. A quality control system for selection of high-producing, non-genetic, metabolic variants of *Escherichia coli* (E. coli) host cells, the system comprising:
  a culture medium; and
  a population of transformed E. coli host cells, each transformed host cell comprising a product-responsive transcription factor selected from the group consisting of FadR, TyrR, BenM, AIkS, Xy1 R, CdaR, FapR, BadR, MarR, EmrR, CbaR, MetJ, GR, NagC, CynR, BmoR, NodD, MdcR, CatR, theophylline riboswitch, ammeline riboswitch, thiamine pyrophosphate riboswitch, and AdoCbl riboswitch and a nucleic acid molecule comprising:
    a promoter operably linked to an antibiotic resistance gene, wherein the promoter is selected from the group consisting of $P_{AR}$, $P_{BAD}$, $P_{LacUV5}$, $P_{mtr}$, $P_{T1}$, and $P_{T2}$; and
    a product-responsive transcription factor binding site operably linked to the promoter, wherein the product-responsive transcription factor binding site binds to the product-responsive transcription factor;
      wherein when the product-responsive transcription factor binds to the product-responsive transcription factor binding site in the absence of a product, promotor activity is repressed and expression of the antibiotic resistance gene is blocked; and
      wherein when the product-responsive transcription factor binds to the product-responsive transcription factor binding site in the presence of the product, promotor activity is activated and the antibiotic resistance gene is expressed.

7. The system of claim 6, wherein the product-responsive transcription factor regulates expression of the selection gene under an applied selection pressure.

8. The system of claim 7, wherein the applied selection pressure comprises an antibiotic-amended cell culture medium.

* * * * *